US012016557B2

(12) United States Patent
Abramek et al.

(10) Patent No.: US 12,016,557 B2
(45) Date of Patent: Jun. 25, 2024

(54) SEALED ELECTRICAL CONNECTION BETWEEN SURGICAL LOADING UNIT AND ADAPTER

(71) Applicant: Covidien LP, Mansfield, MA (US)

(72) Inventors: Pawel Abramek, Berlin, CT (US); Kenneth H. Whitfield, North Haven, CT (US); Roanit A. Fernandes, Hyderabad (IN); Kenneth M. Cappola, Monroe, CT (US)

(73) Assignee: Covidien LP, Mansfield, MA (US)

( * ) Notice: Subject to any disclaimer, the term of this patent is extended or adjusted under 35 U.S.C. 154(b) by 519 days.

(21) Appl. No.: 17/321,855

(22) Filed: May 17, 2021

(65) Prior Publication Data

US 2021/0386424 A1 Dec. 16, 2021

Related U.S. Application Data

(60) Provisional application No. 63/037,274, filed on Jun. 10, 2020.

(51) Int. Cl.
*A61B 17/072* (2006.01)
*A61B 17/00* (2006.01)
(Continued)

(52) U.S. Cl.
CPC ...... *A61B 17/072* (2013.01); *A61B 17/07207* (2013.01); *A61B 2017/00017* (2013.01);
(Continued)

(58) Field of Classification Search
CPC ............... A61B 17/068; A61B 17/072; A61B 17/07207; A61B 17/07292; A61B 17/115;
(Continued)

(56) References Cited

U.S. PATENT DOCUMENTS 2,957,353 A 10/1960 Babacz
3,111,328 A 11/1963 Di Rito et al.
(Continued)

FOREIGN PATENT DOCUMENTS

CA 2451558 A1 1/2003
CN 1547454 A 11/2004
(Continued)

OTHER PUBLICATIONS

Extended European Search Report for U.S. Appl. No. 21/178,601 dated Nov. 8, 2021.
(Continued)

*Primary Examiner* — Scott A Smith
(74) *Attorney, Agent, or Firm* — Carter, DeLuca & Farrell LLP

(57) ABSTRACT

A surgical stapling apparatus includes a housing assembly and an elongated shaft assembly. The elongated shaft assembly is selectively attachable to the housing assembly. The elongated shaft assembly includes an adapter assembly and a loading unit. The adapter assembly extends distally to a distal tip housing. The distal tip housing supports an adapter electrical connector assembly therein. The loading unit is selectively attachable to the adapter assembly and extends distally to an end effector supporting one or more sensors therein. The loading unit supports a loading unit electrical connector assembly therein. The loading unit electrical connector assembly is positioned to contact the adapter electrical connector assembly when the adapter assembly and the loading unit are coupled together to electrically couple the one or more sensors to the housing assembly.

18 Claims, 21 Drawing Sheets

(51) Int. Cl.
*A61B 17/068* (2006.01)
*A61B 90/00* (2016.01)

(52) U.S. Cl.
CPC .......... *A61B 2017/00022* (2013.01); *A61B 2017/00477* (2013.01); *A61B 2017/00486* (2013.01); *A61B 17/068* (2013.01); *A61B 2017/07228* (2013.01); *A61B 2017/07257* (2013.01); *A61B 2017/07271* (2013.01); *A61B 2090/061* (2016.02)

(58) Field of Classification Search
CPC ...... A61B 17/1155; A61B 2017/00017; A61B 2017/00473; A61B 2017/00477; A61B 2017/07219; A61B 2017/07228; A61B 2017/2927
USPC .............. 227/19, 176.1, 175.1, 175.2, 180.1; 606/1, 139, 219
See application file for complete search history.

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,915,616 A | 6/1999 | Viola et al. |
| 5,954,259 A | 9/1999 | Viola et al. |
| 5,964,394 A | 10/1999 | Robertson |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,128,253 B2 | 10/2006 | Mastri et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |

(56) References Cited

U.S. PATENT DOCUMENTS

| | | |
|---|---|---|
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,334,717 B2 | 2/2008 | Rethy et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,070,033 B2 | 12/2011 | Milliman et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,256,656 B2 | 9/2012 | Milliman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |

(56) References Cited

U.S. PATENT DOCUMENTS

| | | |
|---|---|---|
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,713,470 B2 | 7/2017 | Scirica et al. |
| 10,376,263 B2* | 8/2019 | Morgan ............ A61B 17/07207 |
| 10,524,790 B2* | 1/2020 | Shelton, IV ......... A61B 17/115 |
| 10,548,600 B2* | 2/2020 | Shelton, IV ......... A61B 17/105 |
| 10,575,868 B2* | 3/2020 | Hall ..................... A61B 17/072 |
| 10,687,813 B2* | 6/2020 | Shelton, IV ..... A61B 17/07207 |
| 10,702,266 B2* | 7/2020 | Parihar .............. A61B 17/1155 |
| 10,743,875 B2* | 8/2020 | Shelton, IV ..... A61B 17/07207 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |

(56) References Cited

U.S. PATENT DOCUMENTS

| | | |
|---|---|---|
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2018/0064438 A1 | 3/2018 | Zergiebel et al. |
| 2019/0000476 A1* | 1/2019 | Shelton, IV ....... A61B 18/1445 |
| 2019/0000525 A1* | 1/2019 | Messerly ......... A61B 17/07207 |
| 2019/0183493 A1* | 6/2019 | Shelton, IV ..... A61B 17/07207 |
| 2019/0201027 A1 | 7/2019 | Shelton, IV et al. |
| 2019/0290271 A1* | 9/2019 | Scott ................ A61B 17/07292 |
| 2019/0290308 A1* | 9/2019 | Worthington ...... H01R 13/2407 |
| 2019/0388091 A1 | 12/2019 | Eschbach et al. |

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2815705 A1 | 12/2014 |
| ES | 2333509 A1 | 2/2010 |
| FR | 2861574 A1 | 5/2005 |
| JP | 2005125075 A | 5/2005 |
| KR | 20120022521 A | 3/2012 |
| WO | 2011108840 A2 | 9/2011 |
| WO | 2012/040984 A1 | 4/2012 |
| WO | 2016025132 A1 | 2/2016 |

OTHER PUBLICATIONS

Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.

(56) References Cited

OTHER PUBLICATIONS

European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and The Written Opinion of the International Searching Authority issued in corresponding application No. PCT/US2016/027042 dated Jul. 12, 2016.

* cited by examiner

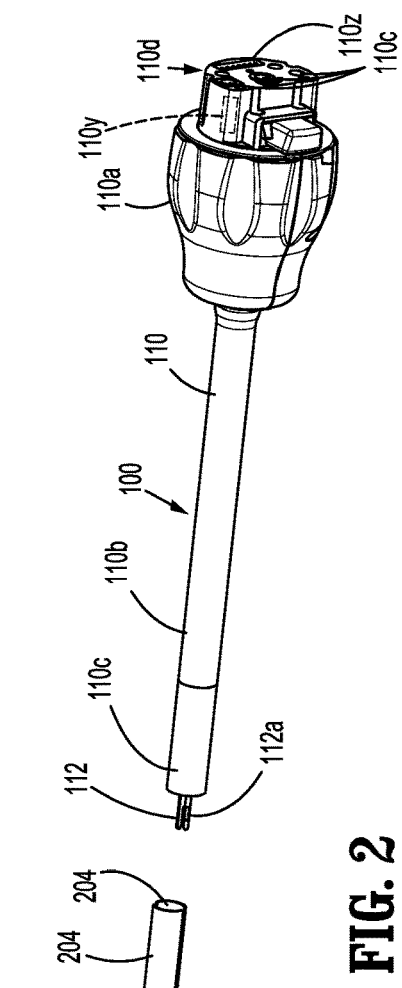
FIG. 2
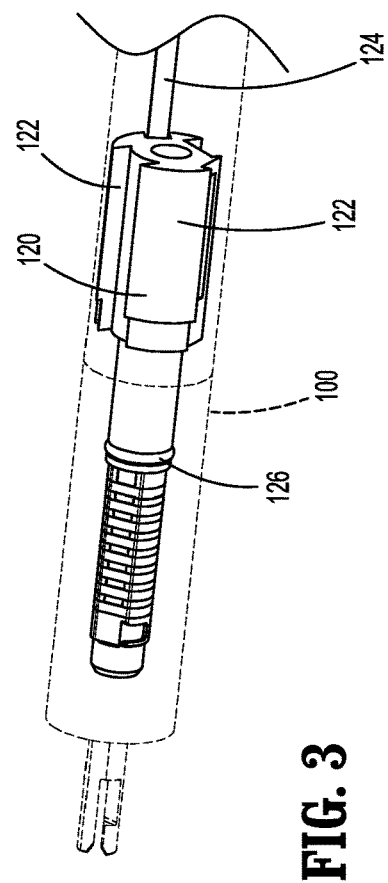
FIG. 3
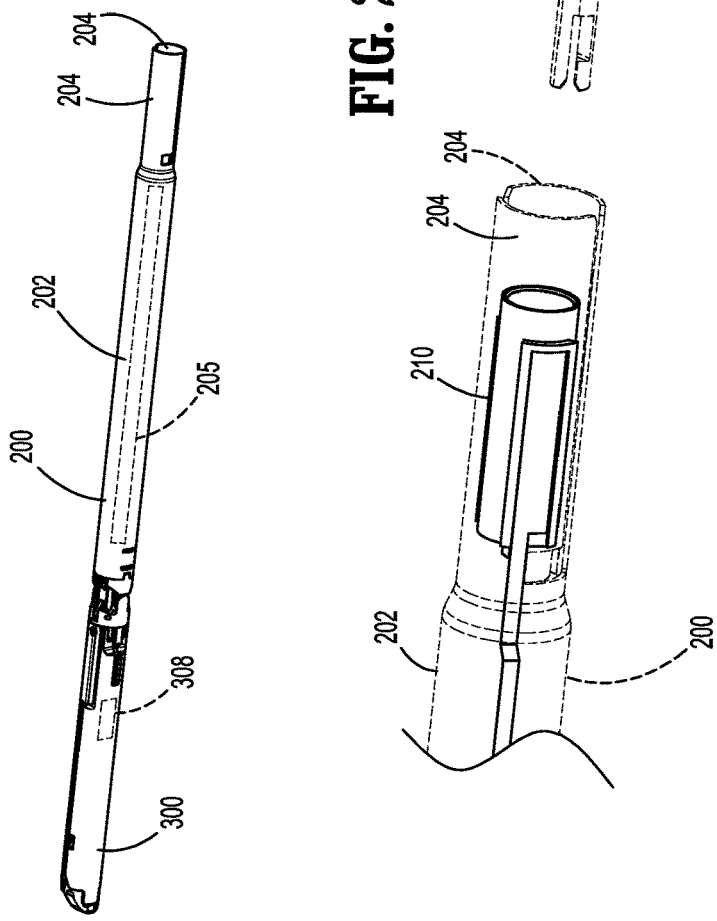

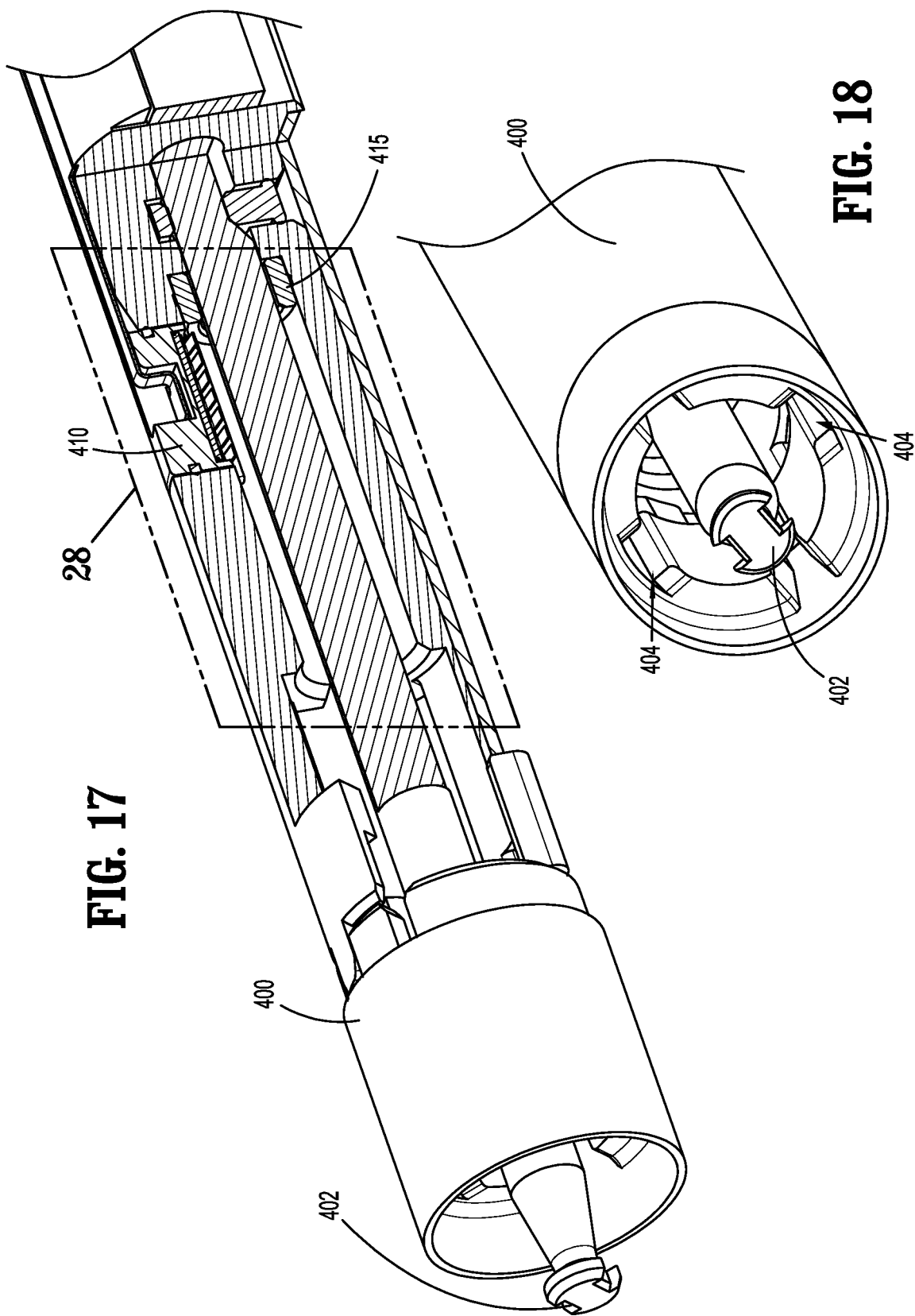

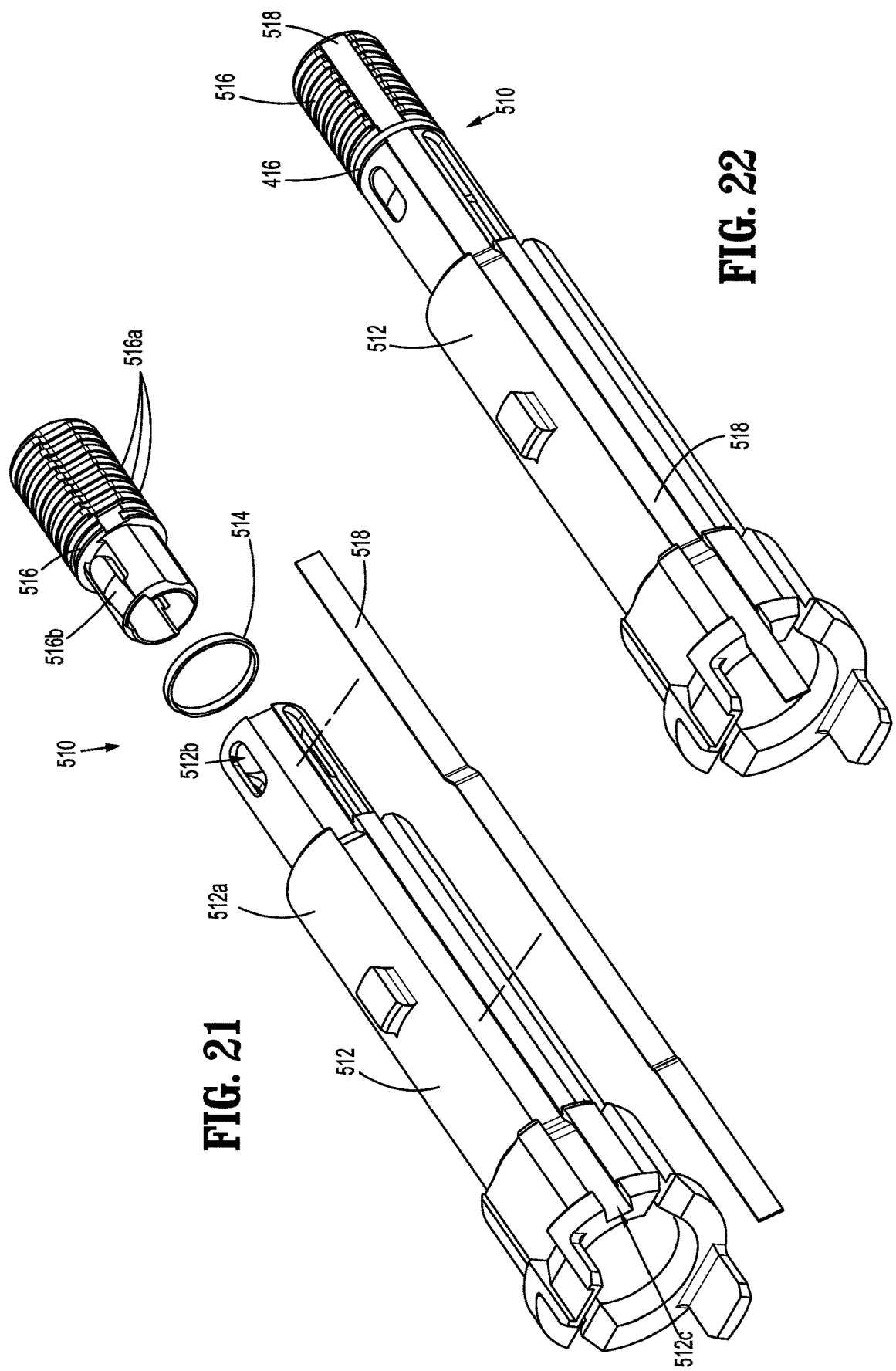

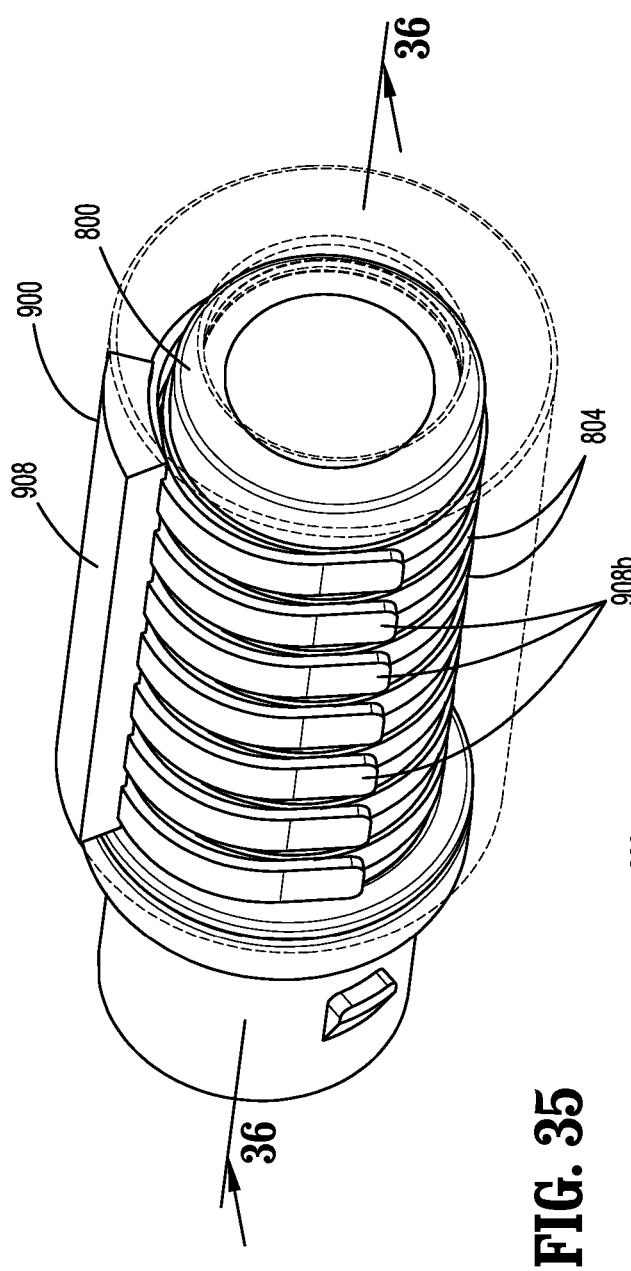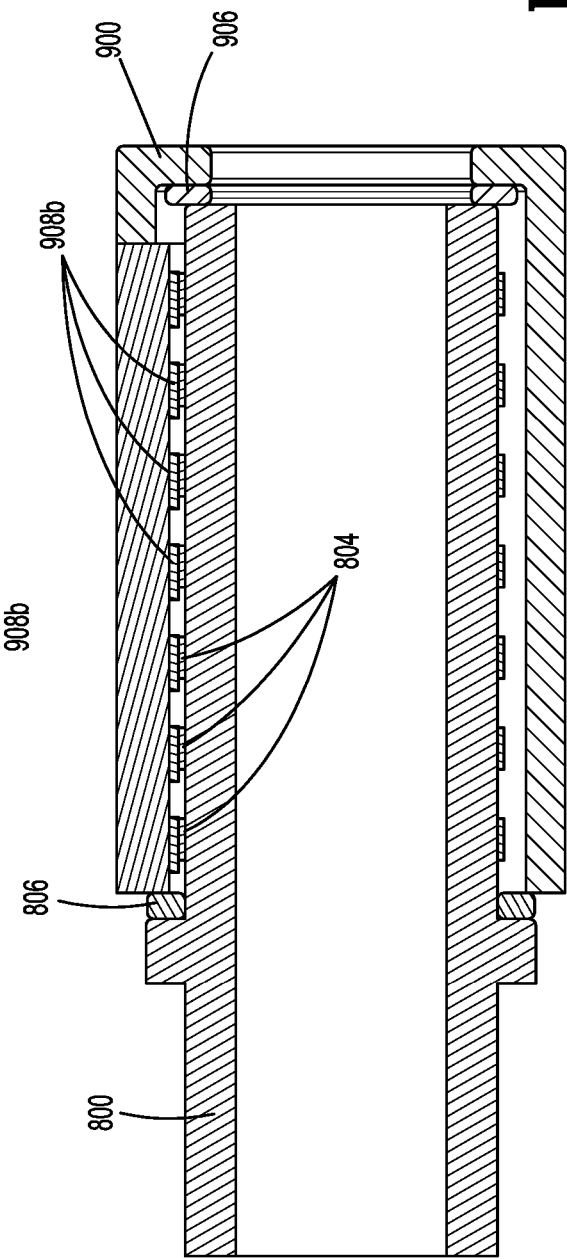

SEALED ELECTRICAL CONNECTION BETWEEN SURGICAL LOADING UNIT AND ADAPTER

CROSS REFERENCE TO RELATED APPLICATIONS

This application claims the benefit of U.S. Provisional Patent Application Ser. No. 63/037,274, filed Jun. 10, 2020, the entire contents of which are hereby incorporated by reference herein.

TECHNICAL FIELD

This disclosure relates to surgical stapling apparatus and, more particularly, to structures and methods for establishing a sealed electrical connection between a surgical loading unit and an adapter of a powered surgical stapling apparatus.

BACKGROUND

Fasteners have traditionally been used to replace suturing when joining various body structures. Surgical stapling apparatus employed to apply these fasteners are generally designed to simultaneously cut and seal tissue to reduce the time and risks involved with surgical procedures. Surgical stapling apparatus that clamp, cut and/or staple tissue are well known in the art. Such surgical stapling apparatus include end effectors having two elongated jaw members used to capture or clamp tissue. These end effectors can be provided in the form of an elongate loading unit removably attachable to a housing assembly via an adapter to enable drive components of the housing assembly to operate the end effector in vivo, for instance, laparoscopically. In particular, one of the two jaw members of the end effector usually carries a staple cartridge that houses a plurality of staples positioned in rows, while the other of the two jaw members has an anvil for forming the staples as the staples are driven from the staple cartridge. In linear surgical stapling apparatus, for example, a stapling operation is effectuated by a cam bar, a drive sled or other similar mechanism having a cam member that travels longitudinally through channels defined in the staple cartridge and acts upon staple pushers in the channels to sequentially eject linear rows of staples from the staple cartridge. A knife is movably positioned between the linear rows of staples such that when the surgical stapling apparatus is positioned about tissue and actuated, the tissue is joined and/or simultaneously or nearly simultaneously cut.

SUMMARY

According to one aspect, a surgical stapling apparatus includes a housing assembly and an elongated shaft assembly. The elongated shaft assembly is selectively attachable to the housing assembly. The elongated shaft assembly includes an adapter assembly and a loading unit. The adapter assembly extends distally to a distal tip housing. The distal tip housing supports an adapter electrical connector assembly therein. The loading unit is selectively attachable to the adapter assembly and extends distally to an end effector supporting one or more sensors therein. The loading unit supports a loading unit electrical connector assembly therein. The loading unit electrical connector assembly is positioned to contact the adapter electrical connector assembly when the adapter assembly and the loading unit are coupled together to electrically couple the one or more sensors to the housing assembly.

In aspects, the one or more sensors may be configured to measure data including thickness of tissue clamped by the end effector, clamp force of the end effector, or firing force of the end effector.

In various aspects, the adapter electrical connector assembly may include an adapter connector housing that rotatably supports a firing rod therethrough. The adapter electrical connector assembly may include an electronic ring assembly that is supported on the adapter connector housing. The adapter connector housing may include a connector shaft that supports the electronic ring assembly thereon. The connector shaft may define a plurality of annular ribs and a plurality of ring recesses disposed between the annular ribs. The plurality of ring recesses and the plurality of annual ribs may be positioned to support a plurality of contact rings of the electronic ring assembly. The plurality of contact rings may be electrically coupled to a flex cable supported by a channel defined within the adapter connector housing. The loading unit electrical connector assembly may include a loading unit connector housing that supports a plurality of spring contacts positioned to contact the plurality of contact rings of the electronic ring assembly. The plurality of spring contacts may be electrically coupled to the one or more sensors.

In aspects, the adapter electrical connector assembly and the loading unit electrical connector assembly may be sealed within elongated shaft assembly when electrically coupled together.

According to yet another aspect, a surgical stapling apparatus includes a housing assembly, an adapter assembly, and a loading unit. The adapter assembly is removably secured to the housing assembly and supports an adapter electrical connector assembly therein. The loading unit is selectively electrically connectable to the adapter assembly by relative translating and rotating movement between the loading unit and the adapter assembly. The loading unit supports a loading unit electrical connector assembly. The loading unit electrical connector assembly is positioned to receive the adapter electrical connector assembly to cause the adapter assembly and the loading unit to electrically couple together in response to the translating and rotating movement.

In aspects, the loading unit may extend to an end effector. The end effector may support one or more sensors disposed in electrical communication with the adapter electrical connector assembly when the loading unit and the adapter assembly are coupled together.

In various aspects, the loading unit may define a lug channel positioned to receive a lug of the adapter assembly. The lug channel may have a longitudinally-extending portion to enable translating movement of the lug therethrough and a transverse portion to enable rotating movement of the lug therethrough.

Other aspects, features, and advantages will be apparent from the description, the drawings, and the claims that follow.

BRIEF DESCRIPTION OF DRAWINGS

The accompanying drawings, which are incorporated in and constitute a part of this specification, illustrate aspects of the disclosure and, together with a general description of the disclosure given above and the detailed description given below, serve to explain the principles of this disclosure, wherein:

FIG. 2 is a perspective view of the elongated shaft assembly of FIG. 1B with the loading unit and the adapter thereof shown separated from one another;

FIG. 3 is an enlarged, perspective view of a proximal end portion of the loading unit and a distal end portion of the adapter, the proximal end portion of the loading unit and the distal end portion of the adapter shown with portions thereof removed and/or in phantom for clarity;

FIG. 17 is an enlarged, perspective view, in partial cross-section, of the distal end portion of the adapter of FIG. 16;

FIG. 18 is a perspective view of the distal end portion of the adapter of FIG. 16;

FIG. 21 is an enlarged, perspective view, with parts separated, of an electrical connector assembly of the loading unit of FIG. 16;

FIG. 22 is a perspective view of the electrical connector assembly of FIG. 21, with parts assembled;

FIG. 35 is an enlarged, perspective view illustrating the loading unit and the adapter of FIG. 33 coupled together; and FIG. 36 is a cross-sectional view of the proximal end portion of the loading unit of FIG. 33 and the distal end portion of the adapter of FIG. 33 coupled together as taken along section line 36-36 shown in FIG. 35.

DETAILED DESCRIPTION

Figure 1A:
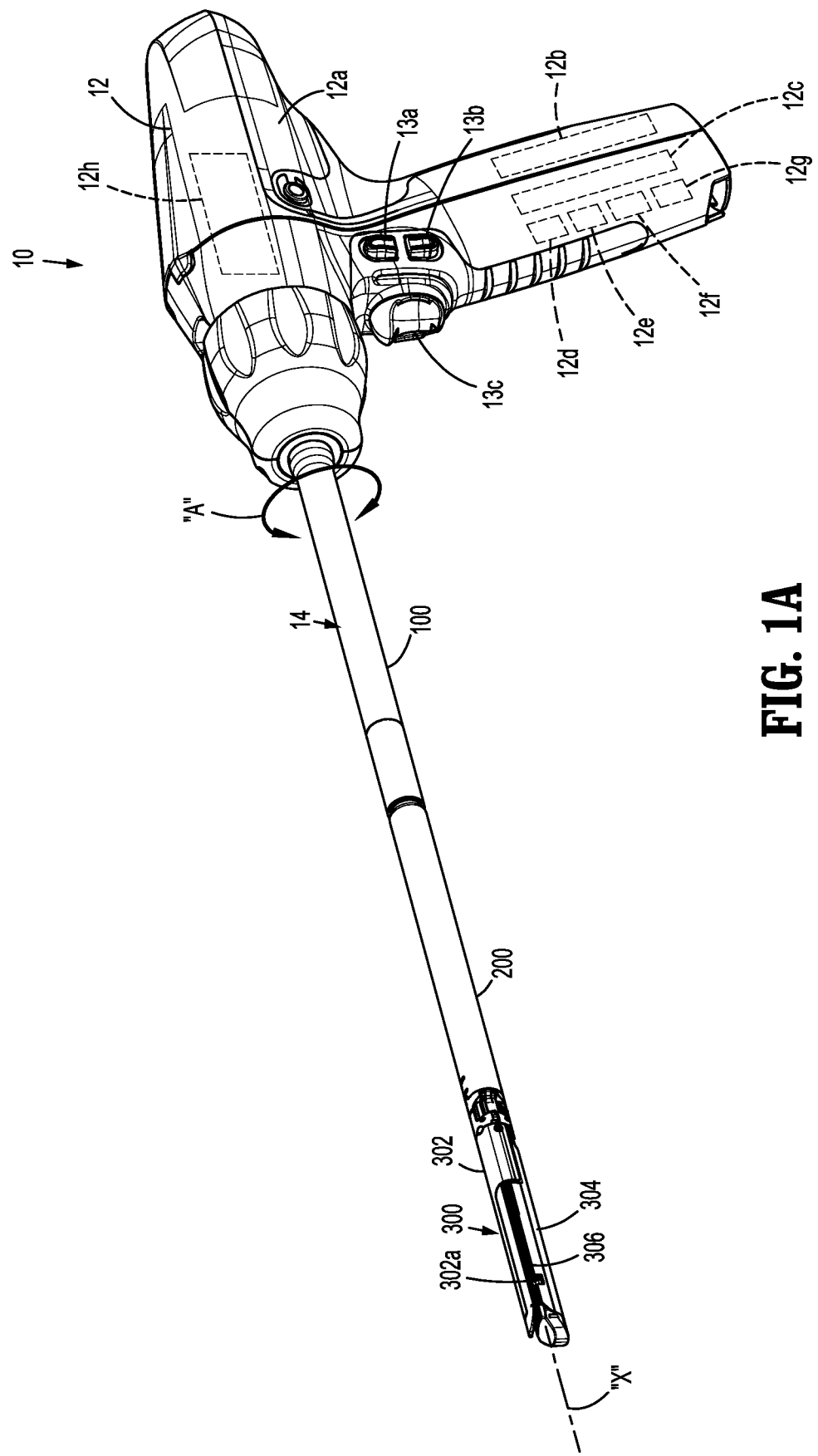
FIG. 1A is a perspective view of an exemplary surgical stapling apparatus in accordance with the principles of this disclosure.

Aspects of the disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

Further, although the surgical instrument described herein is provided in connection with a powered laparoscopic surgical stapling apparatus for brevity, the disclosed surgical instrument can include any powered, manual, or robotically-controlled surgical instruments such as a clip applier, stitching device, energy-based device (e.g., a bipolar or monopolar forceps) or the like, and/or other surgical stapling apparatus such as a circular stapler, a transverse stapler, or an open stapler. For a detailed description of the structure and function of exemplary surgical stapling apparatus, one or more components of which may be included, or modified for use with the disclosed aspects, reference may be made to U.S. Pat. Nos. 9,713,470; 8,806,973; 8,256,656; 8,157,152; 8,070,033 7,819,896; 7,770,774; 7,334,717; 7,128,253; 5,964,394; and 5,915,616, the entire contents of each of which are incorporated herein by reference.

Briefly, due to minerals, ions, etc. in bodily fluids, bodily fluids can be electrically conductive. This disclosure details mechanical structure and methods for securing (and sealing)

an electrical connection that resists contamination from body fluids and saline to prevent electronics of the disclosed surgical stapling apparatus from short circuiting. More specifically, this disclosure details structure and methods for effectively relaying information/data (e.g., continuously) from one or more sensors in an end effector of a surgical stapling apparatus at a distal end portion thereof to a housing or handle assembly at a proximal end portion thereof to accurately determine and/or analyze, for example, tissue thickness, clamp force, firing force, etc. using high speed data transfer speeds and a robust sensor signal (e.g., a strain gauge signal).

Figure 1B:
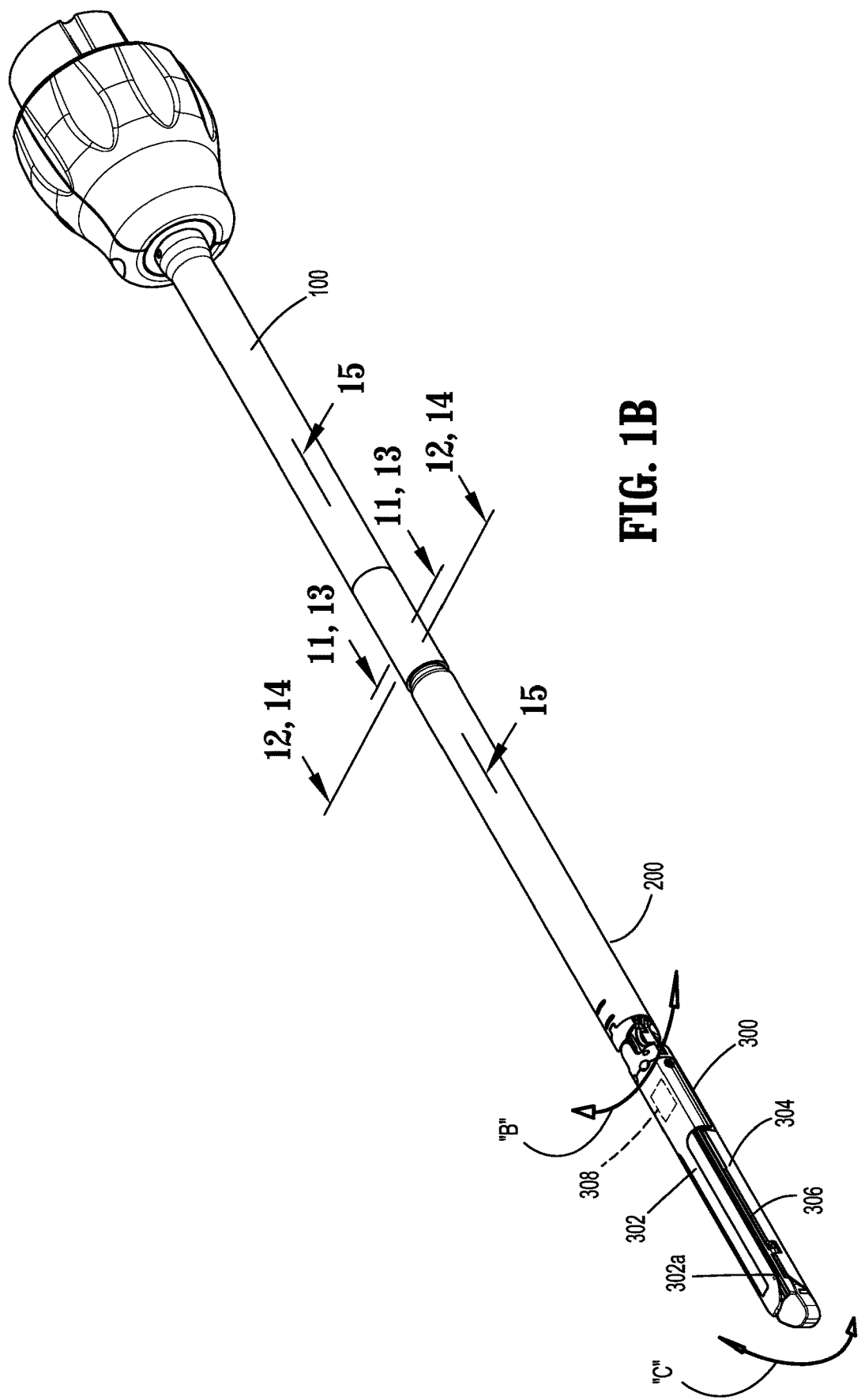
FIG. 1B is a perspective view of an elongated shaft assembly of the surgical stapling apparatus of FIG. 1A, the elongated shaft assembly including a loading unit and an adapter shown coupled together.
Figure 4:
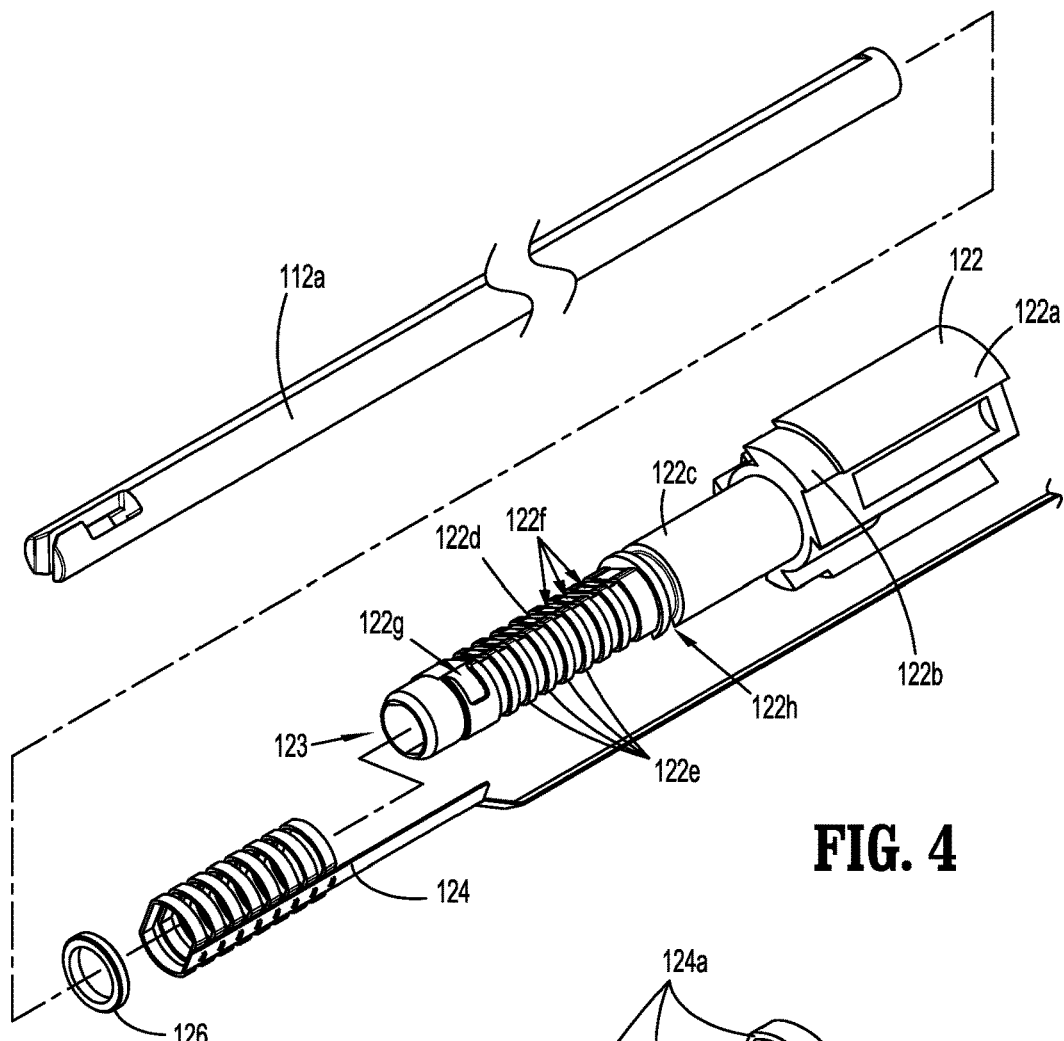
FIG. 4 is an enlarged, perspective view, with parts separated, of a firing rod and an electrical connector assembly of the distal end portion of the adapter.
Figure 5:
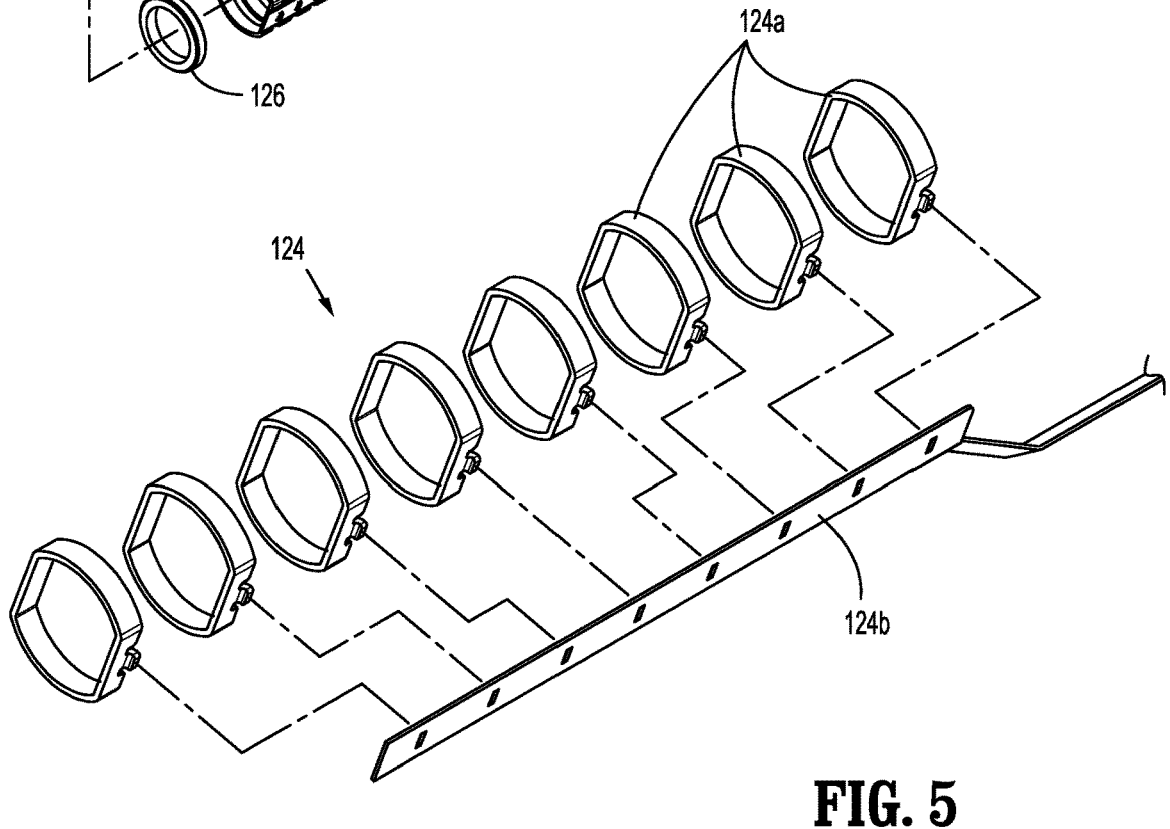
FIG. 5 is an enlarged, perspective view, with parts separated, of portions of the electrical connector assembly of FIG. 4.

With reference to FIGS. 1A and 1B, a surgical stapling apparatus 10 of this disclosure includes a housing assembly 12 (which may include one or more handles that may be manually actuatable to fire surgical stapling apparatus 10) and an elongated shaft assembly 14 that is removably secured to housing assembly 12. Elongated shaft assembly 14 extends distally to housing assembly 12 and defines a longitudinal axis "X" therealong. Elongated shaft assembly 14 includes an adapter assembly 100 having a proximal end portion removably secured to housing assembly 12. Elongated shaft assembly 14 further includes a loading unit 200 that is removably secured to a distal end portion of adapter assembly 100 and which extends distally from adapter assembly 100 to an end effector 300. Loading unit 200 may be disposable and/or include one or more disposable components. End effector 300 of loading unit 200 includes an anvil assembly 302 and a cartridge assembly 304 that houses a plurality of staples (not shown) in a reload or cartridge 306 thereof that may be selectively replaceable. Anvil assembly 302 includes an anvil 302a against which the plurality of staples is formed upon a firing of surgical stapling apparatus 10. End effector 300 further includes one or more sensors 308 disposed in electrical communication with housing assembly 12. Sensors 308 may include, for example, a strain gauge, a cartridge ID sensor, a near field communications (NFC) antenna, etc. Sensors 308 may be disposed within one or both of anvil assembly 302 and cartridge assembly 304. Sensors 308 are configured to electrically communicate with housing assembly 12 regarding data/information regarding the end effector 300 and/or tissue engaged by end effector 300. For instance, such data/information may relate to tissue thickness, clamp force, firing force, etc.

Housing assembly 12 of surgical stapling apparatus 10 includes a housing 12a configured for selective removable receipt of a rechargeable battery 12b. Battery 12b is configured to supply power to electrical components of surgical stapling apparatus 10. Housing 12a supports a controller 12c (e.g., a circuit board) therein that is configured to control various operations of surgical stapling apparatus 10, and which includes any number of electronic components such as memory 12d, a processor 12e, a network interface 12f, and/or other input/output modules 12g. Controller 12c may be coupled to a local or remote display device (not shown) for outputting information and/or data such as a condition of components of surgical stapling apparatus 10 and/or tissue grasped by end effector 300.

Surgical stapling apparatus 10 further includes a drive mechanism 12h configured to drive mechanical and/or electrical components such as rotatable shafts and/or gear components (not shown) within housing 12a in order to perform various operations of surgical stapling apparatus 10. For instance, drive mechanism 12h may be operable to selectively rotate and/or articulate end effector 300 about, and/or relative to, the longitudinal axis "X" of surgical stapling apparatus 10, as indicated by arrows "A" and "B," respectively; to selectively move anvil assembly 302 relative to the cartridge assembly 301 and/or vice versa, as indicated by arrows "C" to selectively clamp tissue; and/or to fire surgical stapling apparatus 10 for fastening and/or cutting the clamped tissue. Battery 12b, controller 12c, and/or drive mechanism 12h may be operably coupled to one or more actuators 13a, 13b, and 13c such as finger-actuated control buttons, rocker devices, and/or the like to effectuate various functions of surgical stapling apparatus 10 such as those described above.

Figure 6:
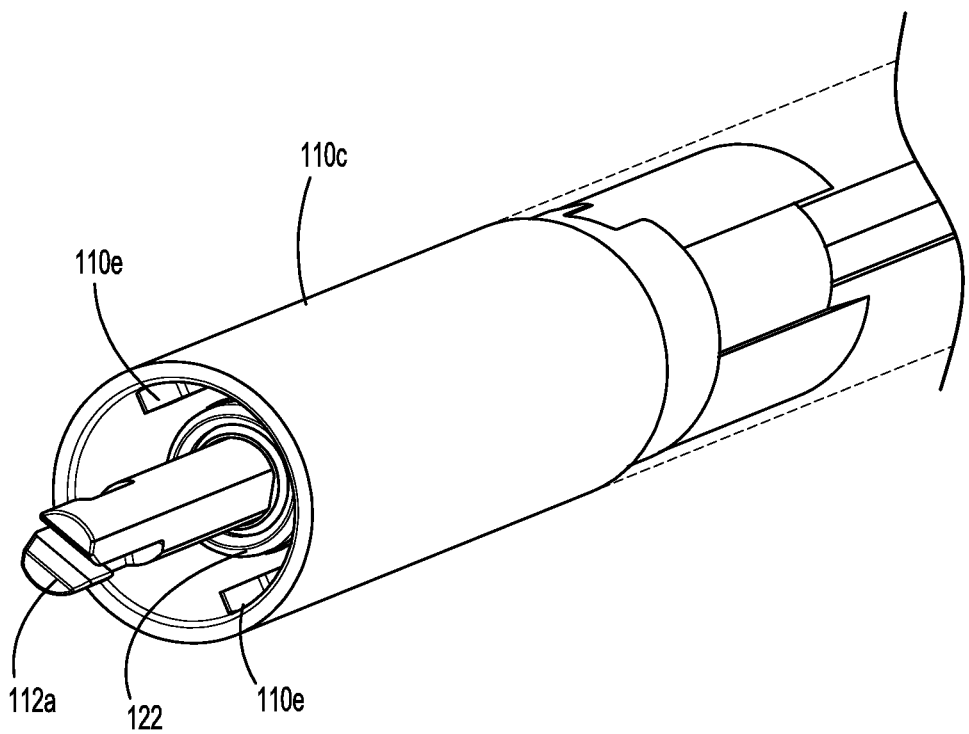
FIGS. 6 and 7 are enlarged, perspective views of the distal end portion of the adapter with portions thereof removed and/or in phantom for clarity.
Figure 7:
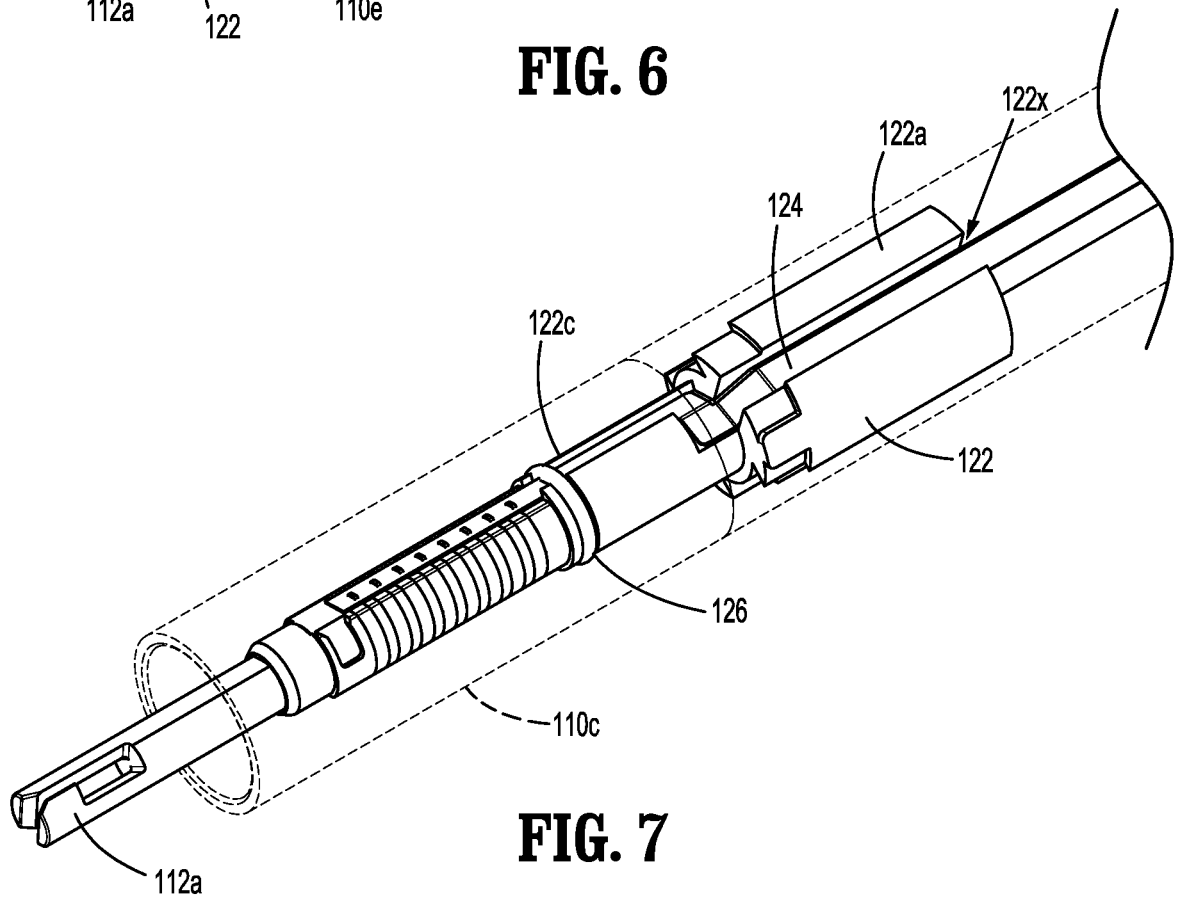
Figure 8:
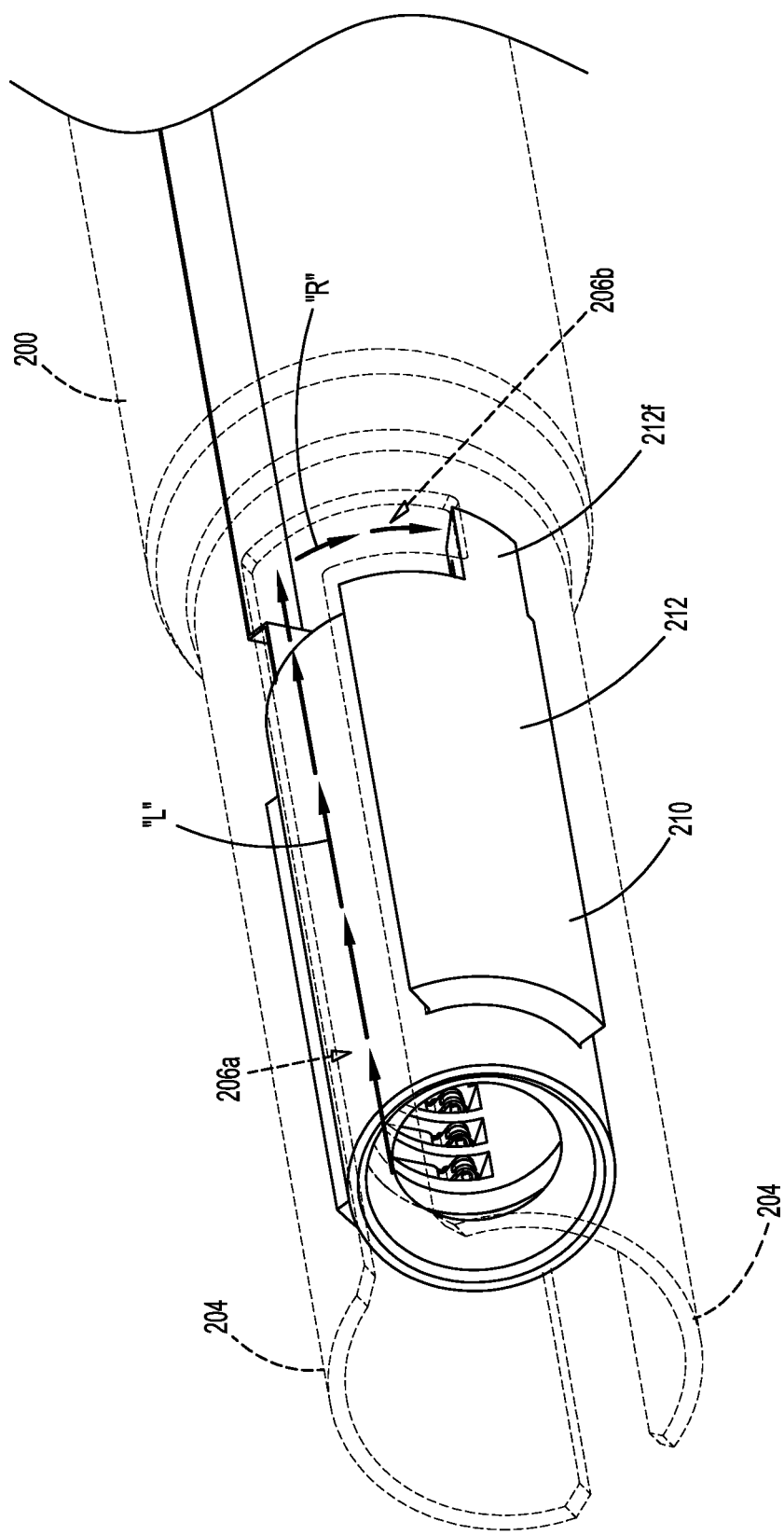
FIG. 8 is an enlarged, perspective view of the proximal end portion of the loading unit with portions thereof removed and/or in phantom for clarity.
Figure 9:
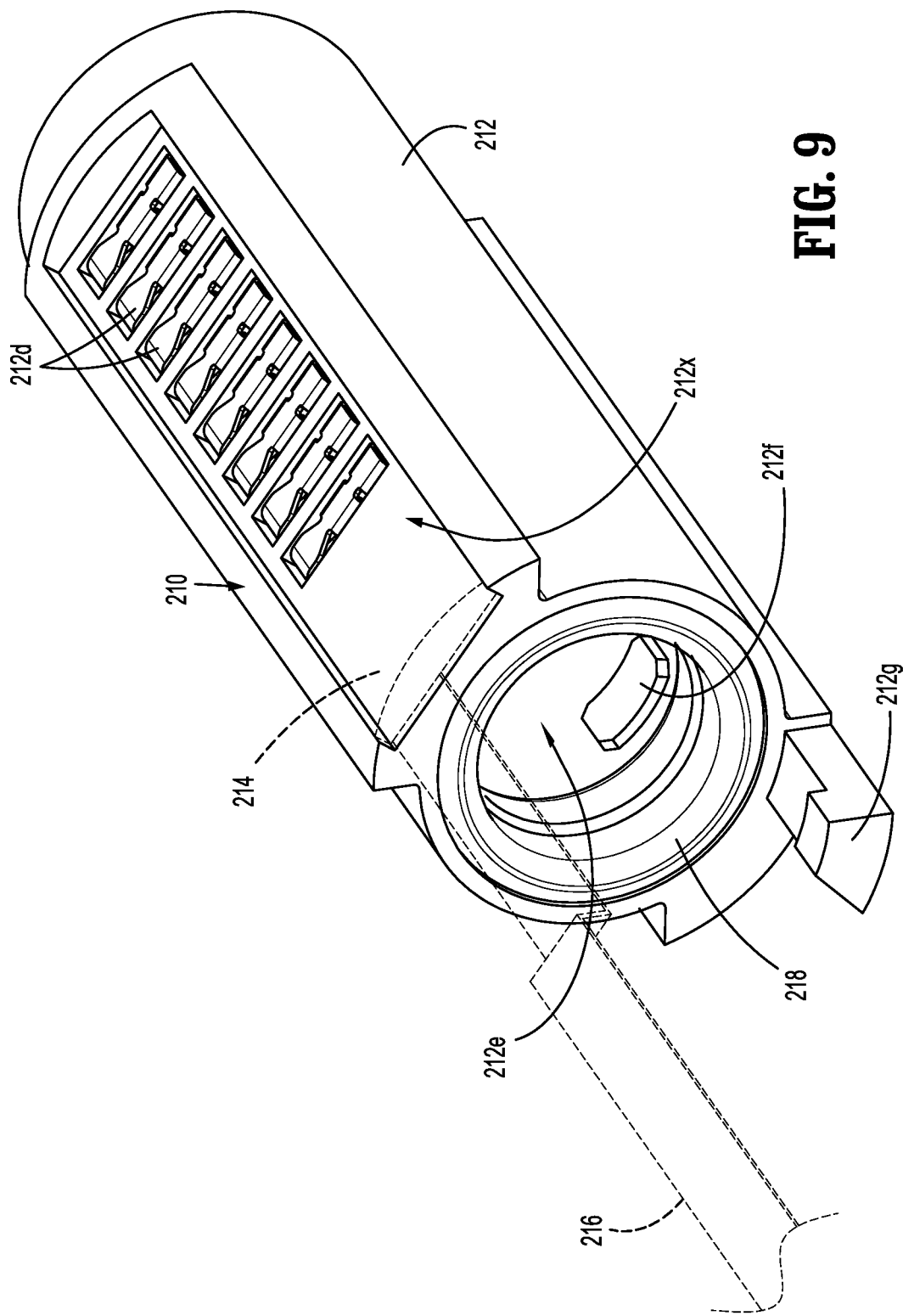
FIG. 9 is an enlarged, perspective view of an electrical connection assembly of the loading unit with portions thereof in phantom for clarity.
Figure 10:
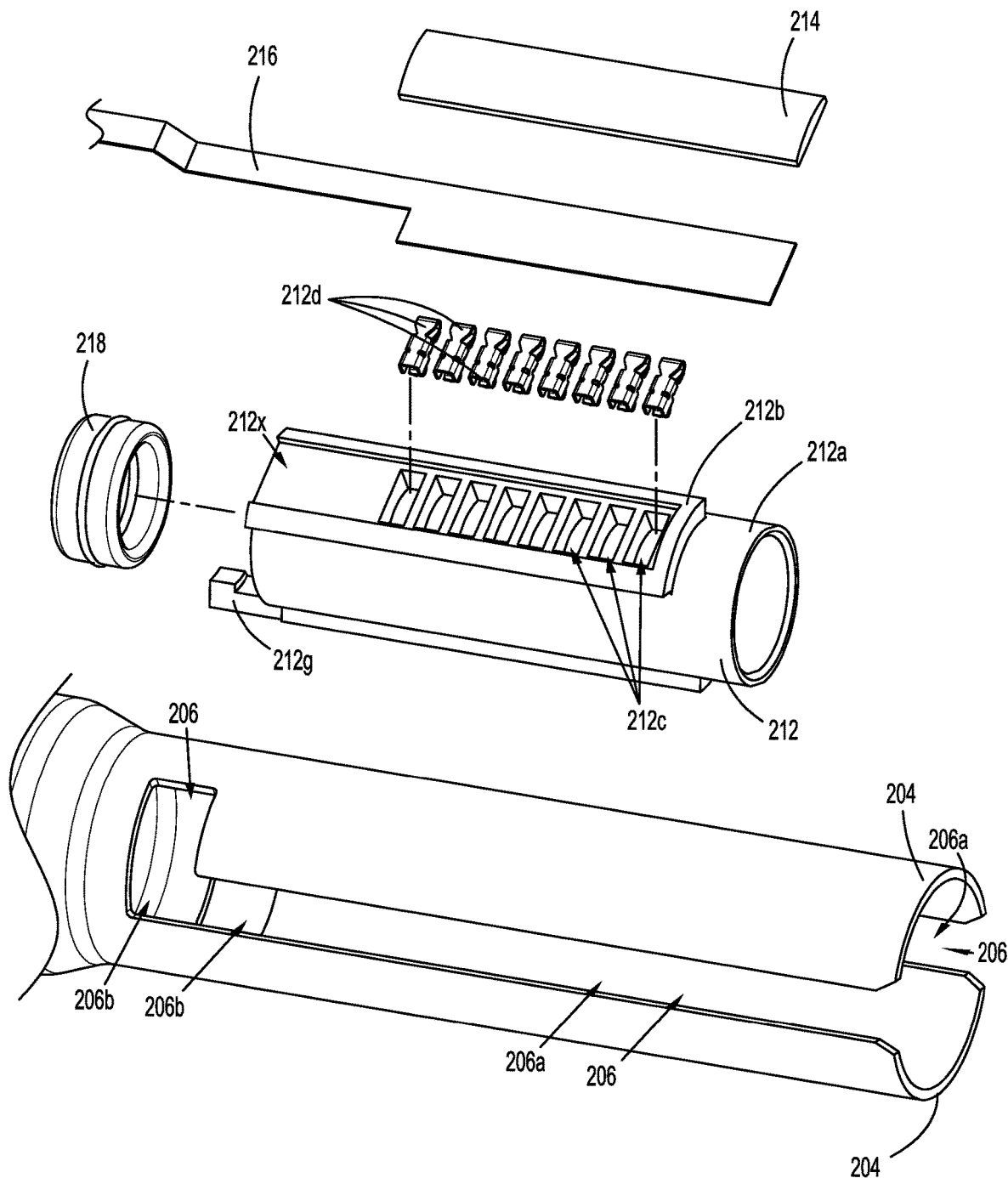
FIG. 10 is a perspective view, with parts separated, of the electrical connection assembly of FIG. 9 and a proximal end portion of an outer tube of the loading unit.
Figure 11:
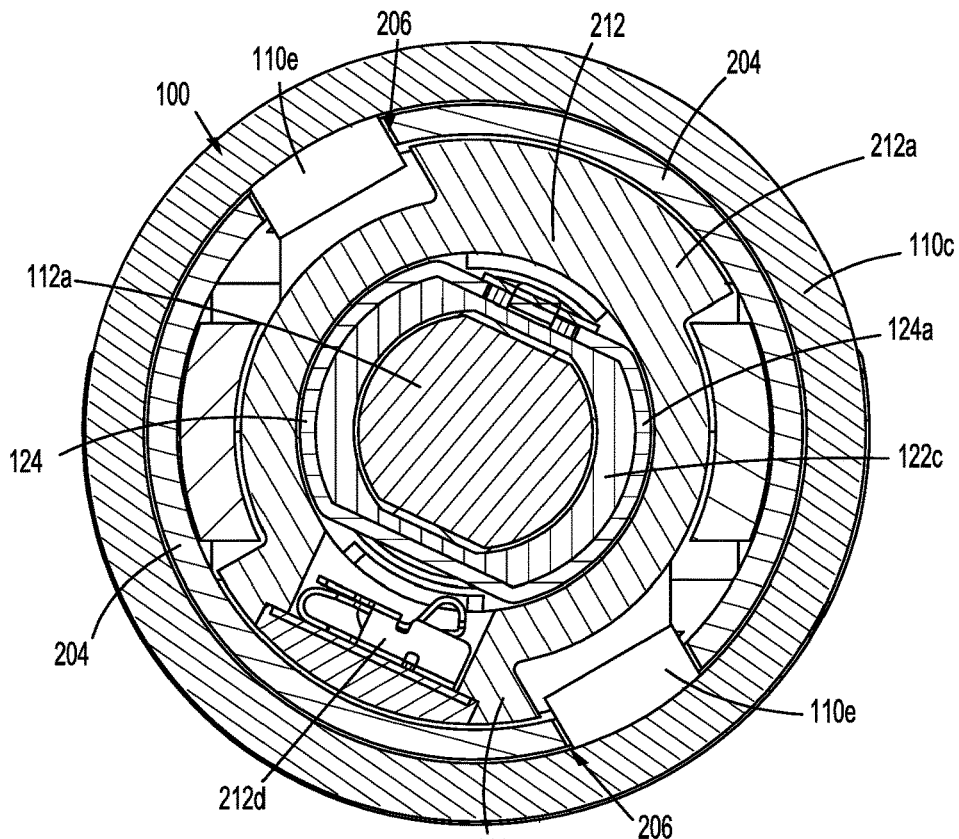
FIGS. 11-15 are enlarged, progressive cross-sectional views of the elongated shaft assembly as taken along respective section lines 11-11, 12-12, 13-13, 14-14, and 15-15 shown in FIG. 1B, these views illustrating the loading unit and the adapter being coupled together.
Figure 12:
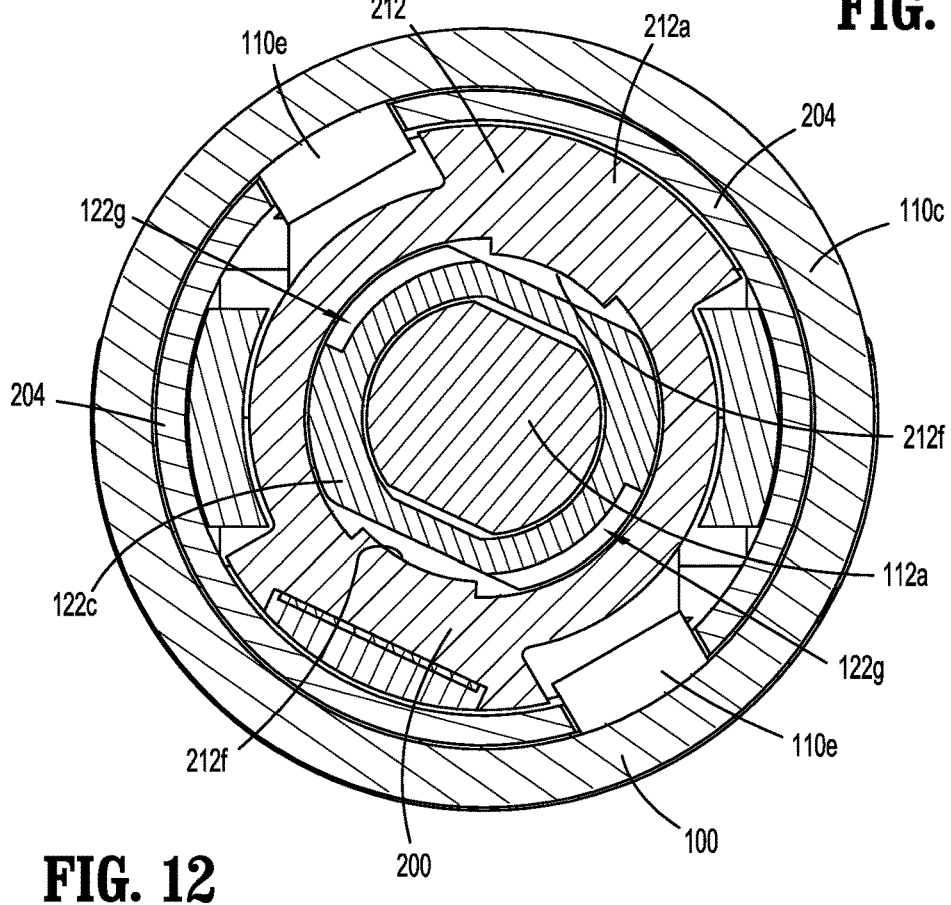
Figure 13:
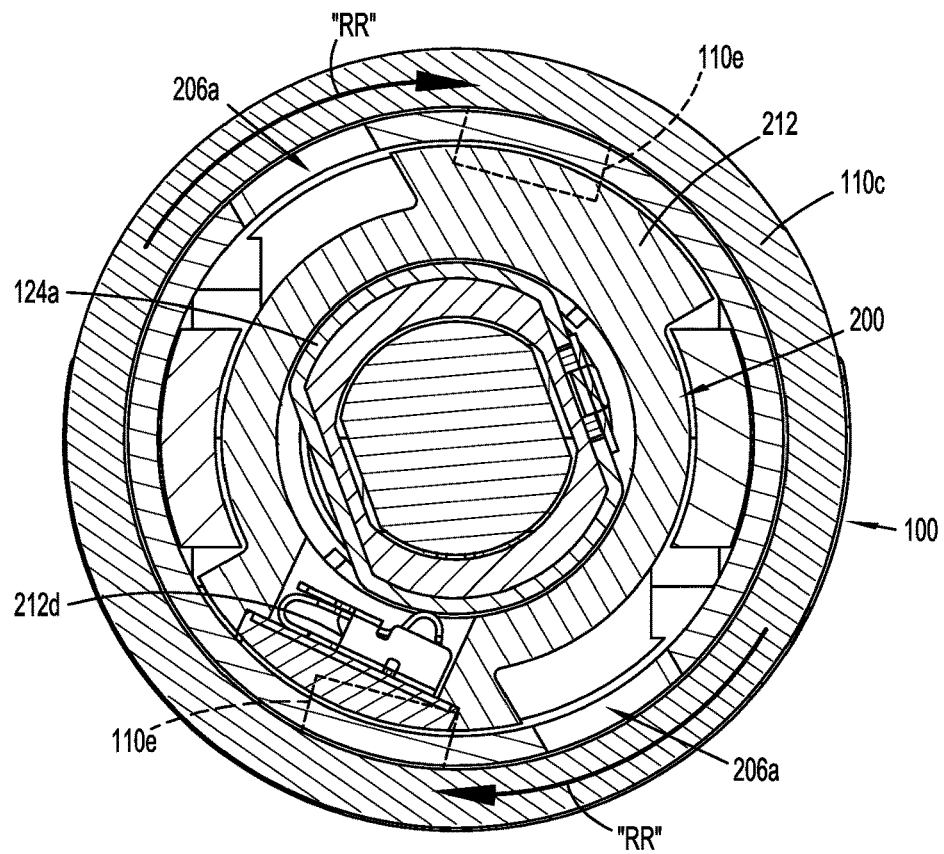
Figure 14:
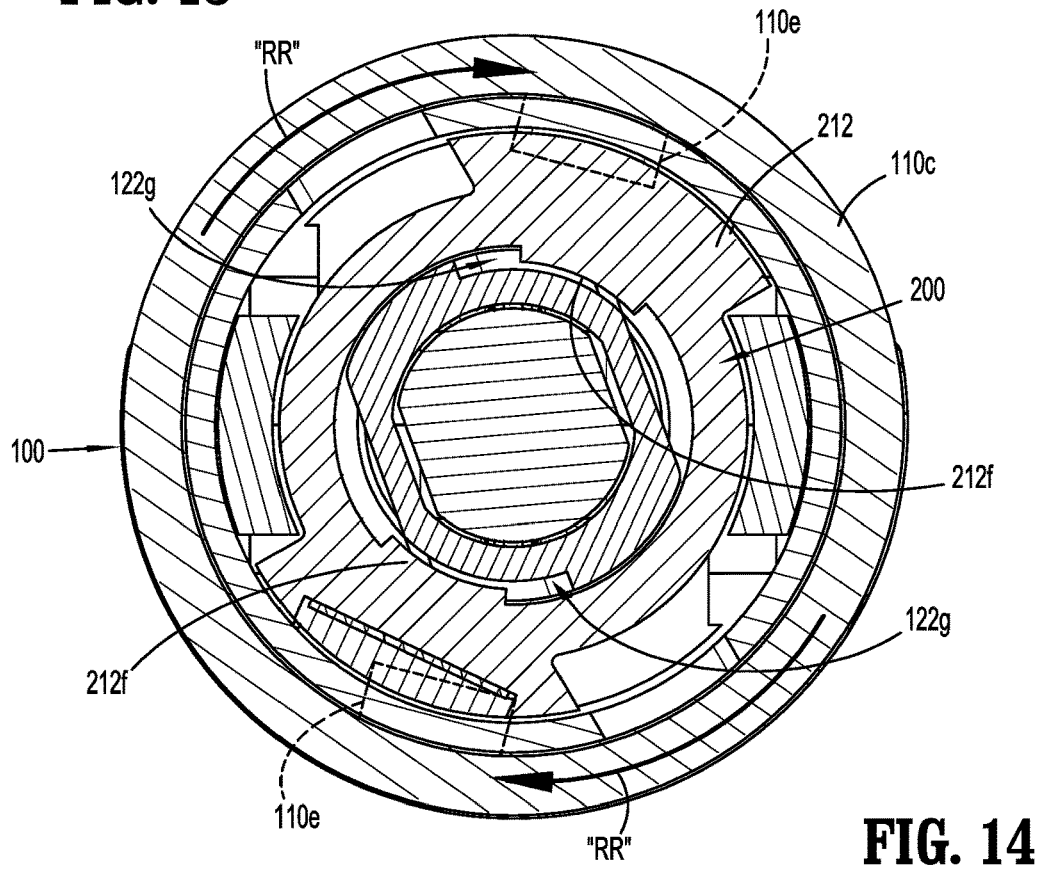

Turning now to FIGS. 2-15, adapter assembly 100 of elongated shaft assembly 14 includes an outer housing 110 and supports a drive assembly 112 therein. Outer housing 110 has a proximal outer housing 110a and a tubular outer housing 110b that extends distally from proximal outer housing 110a to a distal tip housing 110c. Proximal outer housing 110a supports an electrical assembly 110d and a plurality of drive couplers 110c that electromechanically couple to drive mechanism 12h of housing assembly 12. More specifically, electrical assembly 110d includes, for example, an electrical port 110z and a printed circuit board assembly 110y in electrical communication with one another (see FIG. 2). Electrical assembly 110d is configured to electrically communicate with, for example, controller 12c of housing assembly 12 when adapter 100 is coupled to housing assembly 12 while drive couplers 110c mechanically engage drive mechanism 12h, which may include, for instance, a plurality of rotatable actuators (shown) to impart mechanical force (e.g., rotational force) through drive assembly 112 of adapter assembly 100. For example, drive assembly 112 of adapter assembly 100 includes a firing rod 112a that extends distal to distal tip housing 110c and is mechanically engageable with the proximal end portion of loading unit 200 to impart mechanical force (e.g., linear and/or rotational) onto end effector 300 for firing end effector 300 when drive mechanism 12h of housing assembly 12 is actuated. Distal tip housing 110c includes lugs 110e (see FIG. 6) extending radially inward from an inner surface of distal tip housing 110c and positioned to facilitate locking engagement with a proximal end portion of loading unit 200. Lugs 110e may be disposed in diametrically opposed relationship to one another.

Adapter assembly 100 further supports an adapter electrical connector assembly 120 that is disposed in electrical communication with electrical assembly 110d of proximal outer housing 110a. Adapter electrical connector assembly 120 includes an adapter connector housing 122 that is positioned to receive firing rod 112a therethrough so that firing rod 112a is rotatable relative to adapter connector housing 122. Adapter electrical connector assembly 120 further includes an electronic ring assembly 124 and a seal 126 (e.g., an annular seal or gasket such as an O-ring) that are secured to adapter connector housing 122.

As best seen in FIGS. 2-7, adapter connector housing 122 of adapter electrical connector assembly 120 is supported within tubular outer housing 110b of adapter assembly 100. Adapter connector housing 122 includes a proximal base 122a having a distal ledge 122b recessed from proximal base 122a to enable adapter connector housing 122 to couple to a proximal end portion of distal tip housing 110c of adapter assembly 100. Adapter connector housing 122, which may be wholly or partially non-conductive, further includes a connector shaft 122c that extends distally from proximal base 122a for supporting electronic ring assembly 124 and seal 126. Connector shaft 122c and proximal base 122a define a flex channel 122x (see FIG. 7) along an outer surface thereof for supporting electronic ring assembly 124 and a central lumen 123 therethrough for rotatably receiving firing rod 112a therethrough. Connector shaft 122c includes a mounting finger 122d having a plurality of annular ribs 122e that are longitudinally spaced apart along an outer surface of mounting finger 122d to define ring recesses 122f between adjacent annular ribs 122e for receiving electronic ring assembly 124. Connector shaft 122c further defines a pair alignment notches 122g disposed in diametrical opposed relation to one another (see FIGS. 4 and 12) on the outer surface of connector shaft 122c and distal to the plurality of annular ribs 122e to facilitate engagement with loading unit 200 (and to help maintain proper positioning of ribs 122e for isolating electrical contacts). Connector shaft 122c further defines an annular seal channel 122h for mounting seal 126 to adapter connector housing 122 over electronic ring assembly 124 (e.g., overmolded or assembled). Electronic ring assembly 124 includes a plurality of longitudinally spaced apart contact rings 124a, which are conductive (e.g., metallic), that are secured within ring recesses 122f of mounting finger 122d (e.g., insert molded) and are coupled to a connector flex assembly 124b (e.g., soldered) that is supported within flex channel 122x of adapter connector housing 122. Connector flex assembly 124b, which may be in the form of a flex cable for electrically communicating data and/or power, extends proximally from adapter connector housing 122 and is disposed in electrical communication with electrical assembly 110d of adapter assembly 100.

With reference to FIGS. 2, 3, and 8-11, loading unit 200 of elongated shaft assembly 14 has a tubular shaft 202 that supports a loading unit drive assembly 205 therein that is configured to couple to drive assembly 112 of adapter assembly 100 to operate end effector 300. A proximal portion of tubular shaft 202 of loading unit 200 has a pair of curved tines 204 disposed in mirrored relationship with one another (e.g., diametrically opposed) and which extend to a proximal end of loading unit 200. Tines 204 of tubular shaft 202 are receivable within distal tip housing 110c of adapter assembly 100. The curved tines 204 define a pair of outer lug channels 206 for receiving lugs 110e of adapter assembly 100 (see FIG. 6) therein to secure loading unit 200 and adapter assembly 100 together. Outer lug channels 206 of loading unit 200 include a longitudinally-extending portion 206a for longitudinally receiving lugs 110e, as indicated by arrows "L" in FIG. 8, and a transverse portion 206b at a distal end of longitudinally-extending portion 206a for rotatably receiving lugs 110e therein, as indicated by arrows "R" in FIG. 8, to lock loading unit 200 and adapter assembly 100 together.

Loading unit 200 of elongated shaft assembly 14 supports a loading unit electrical connector assembly 210 between the pair of curved tines 204. Loading unit electrical connector assembly 210 extends distally through tubular shaft 202 for electrically coupling to sensors 308 supported within end effector 300, and 210 includes a loading unit connector housing 212 (wholly or partially non-conductive) having a tubular body 212a that supports an outer rail 212b. Outer rail 212b defines a series of spring contact recesses 212c therein. The spring contact recesses 212c are longitudinally spaced apart from one another. Spring contact recesses 212c support a series of spring contacts 212d, which are electrically conductive (e.g., metallic). Outer rail 212b further defines rail channel 212x therein that extends longitudinally along outer rail 212b. Tubular body 212a defines a central passage 212e therethrough and which is configured to receive adapter electrical connector assembly 120 of adapter assembly 100 therein and firing rod 112a of adapter assembly 100 therethrough. Tubular body 212a further includes a pair of tabs 212f (see FIGS. 9 and 12) extending radially inward from an inner surface of tubular body 212a. Tabs 212f are positioned to engage the pair alignment notches 122g defined in connector shaft 122c of adapter connector housing 122 (see FIG. 4) to facilitate securement of loading unit 200 and adapter assembly 100 together. Tubular body 212a further includes a distal tooth 212g which functions as a rotational stop for lugs 110e of adapter assembly 100 (see FIG. 8) and a retention feature that keeps loading unit connector housing 212 engaged with loading unit 200. Loading unit electrical connector assembly 210 further includes a seal cap 214, a loading unit flex assembly 216, which may be in the form of a flex cable, and a seal ring 218 (e.g., an O-ring). Seal cap 214 is mounted in rail channel 212x of outer rail 212b over a backside of loading unit flex assembly 216 and is configured to secure spring contacts 212d within outer rail 212b and to stiffen and seal the backside of loading unit flex assembly 216. Loading unit flex assembly 216 extends distally through loading unit 200 to electrically couple to sensors 308 within end effector 300. Seal ring 218 seats in a distal portion of central passage 212e of tubular body 212a of loading unit electrical connector assembly 210 to seal the central passage 212e of tubular body 212a.

Figure 15:
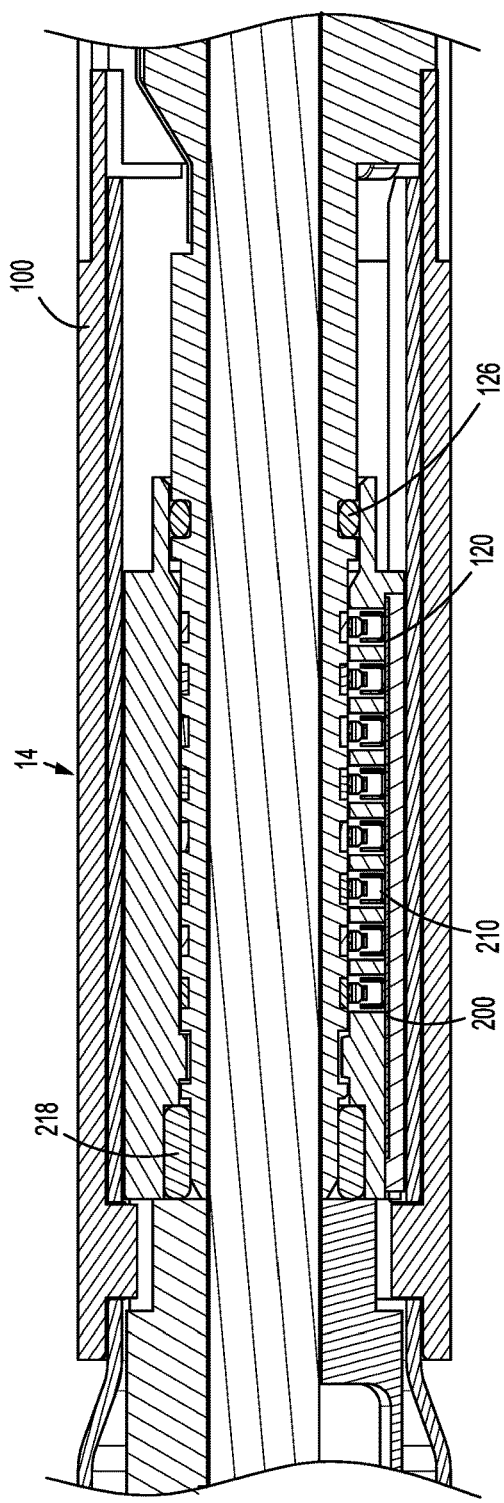
Figure 16:
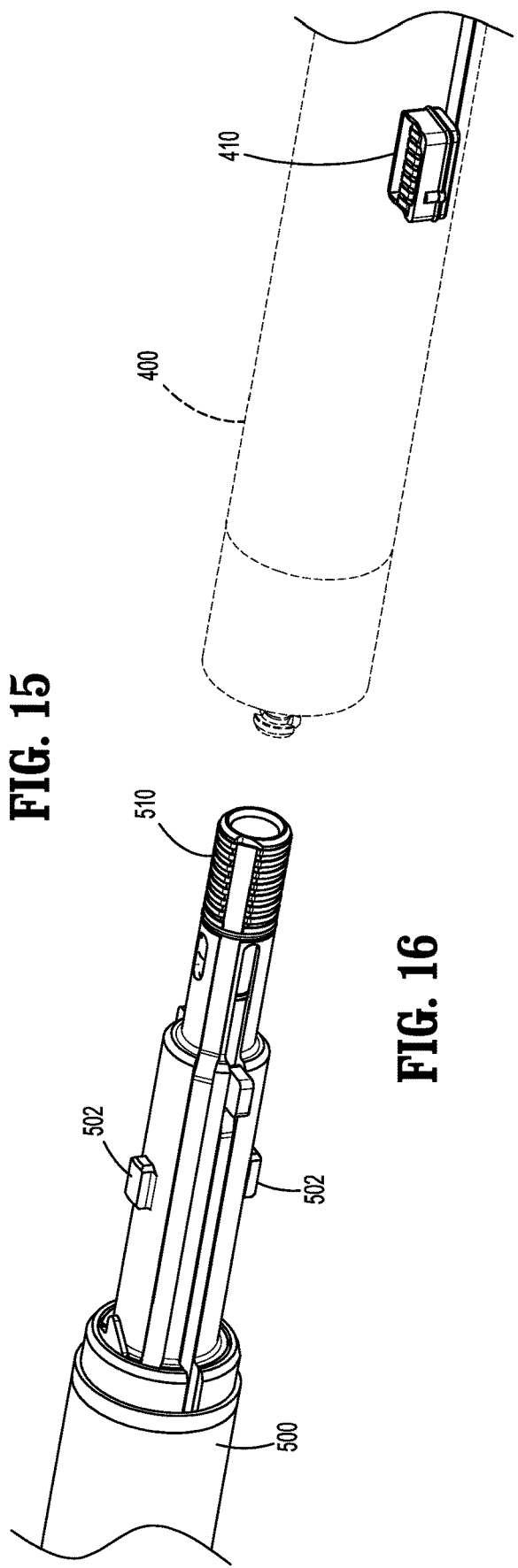
FIG. 16 is a perspective view of a proximal end portion of another loading unit of the of the elongated shaft assembly of FIG. 1B and a distal end portion of another adapter of the elongated shaft assembly of FIG. 1B with portions thereof removed and/or in phantom for clarity.

With reference to FIGS. 8 and 11-15, to mechanical and electrically couple adapter assembly 100 and loading unit 200 together, the curved tines 204 of tubular shaft 202 of loading unit 200 is inserted within distal tip housing 110c of adapter assembly 100 so that lugs 110e of distal tip housing 110c translate distally along outer lug channels 206. Lugs 110e are advanced distally along longitudinally-extending portion 206a of outer lug channel 206, as indicated by arrows "L" (see FIG. 8) until longitudinally aligned with transverse portion 206b of outer lug channel 206, and tabs 212f of tubular body 212a are longitudinally aligned with alignment notches 122g of connector shaft 122c. Then, relative rotation between adapter assembly 100 and loading unit 200, as indicated by arrows "RR" shown in FIGS. 13 and 14, causes lugs 110e to rotate into transverse portion 206b of outer lug channel 206, as indicated by arrows "R" in FIG. 8 and tabs 212f to rotate into alignment notches 122g. In this position, adapter assembly 100 and loading unit 200 are mechanical locked together and electrically coupled together via contact between adapter electrical connector assembly 120 and loading unit electrical connector assembly 210 as seen in FIG. 15 so that an electrical circuit is formed from sensors 308 in end effector 300 through elongated shaft assembly 14, and to housing assembly 12 (e.g., controller 12c, battery 12b, etc., thereof.) In this position, adapter electrical connector assembly 120 and loading unit electrical connector assembly 210 are sealed via seal ring 218 and seal 126.

Once the electrical circuit is created, surgical stapling apparatus 10 can be used to effectuate a surgical procedure, whereby the electrical circuit can determine and/or analyze data/information may relate to tissue thickness, clamp force, firing force, etc. to help facilitate the efficiency and effectiveness of the surgical procedure. Loading unit 200 can be separated and removed from adapter assembly 100 as desired, for example, to dispose of and/or replace the loading unit 200 with another loading unit 200. Adapter assembly 100 is likewise removable and replaceable with respect to loading unit 200 and/or housing assembly 12.

Turning now to FIGS. 16-28, according to another aspect, adapter assembly 400 and a loading unit 500 can also be removably, electromechanically coupled together similar to adapter 100 and loading unit 200. Adapter assembly 400 includes adapter electrical connector assembly 410 and loading unit 500 includes loading unit electrical connector assembly 510. Adapter electrical connector assembly 410 of adapter assembly 400 couples to electrical assembly 110d at the proximal end portion of adapter assembly 400 and loading unit electrical connector assembly 510 couples to sensors 308 supported in end effector 300. Adapter assembly 400 supports a firing rod 402 and defines lug slots 404 therein for receiving lugs 502 extending radially outward from the proximal end portion of loading unit 500. Adapter assembly 400 further includes seal ring 415 supported about firing rod 402 proximal to adapter electrical connector assembly 410.

Figure 19:
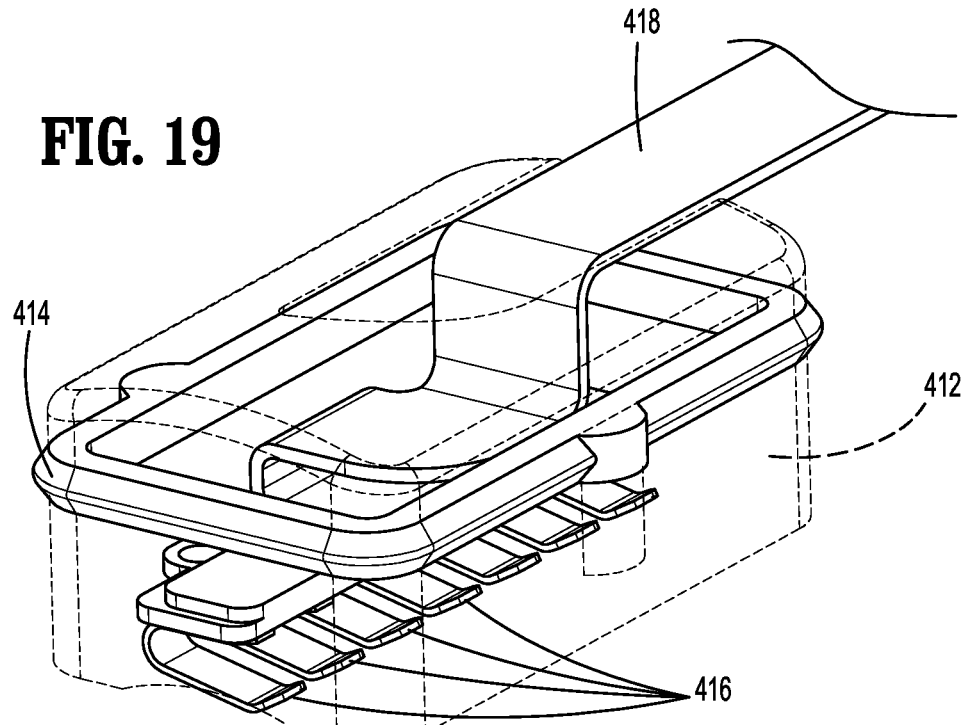
FIG. 19 is an enlarged, perspective view of an electrical connector assembly of the adapter of FIG. 16 with portions of the electrical connector assembly in phantom for clarity.
Figure 20:
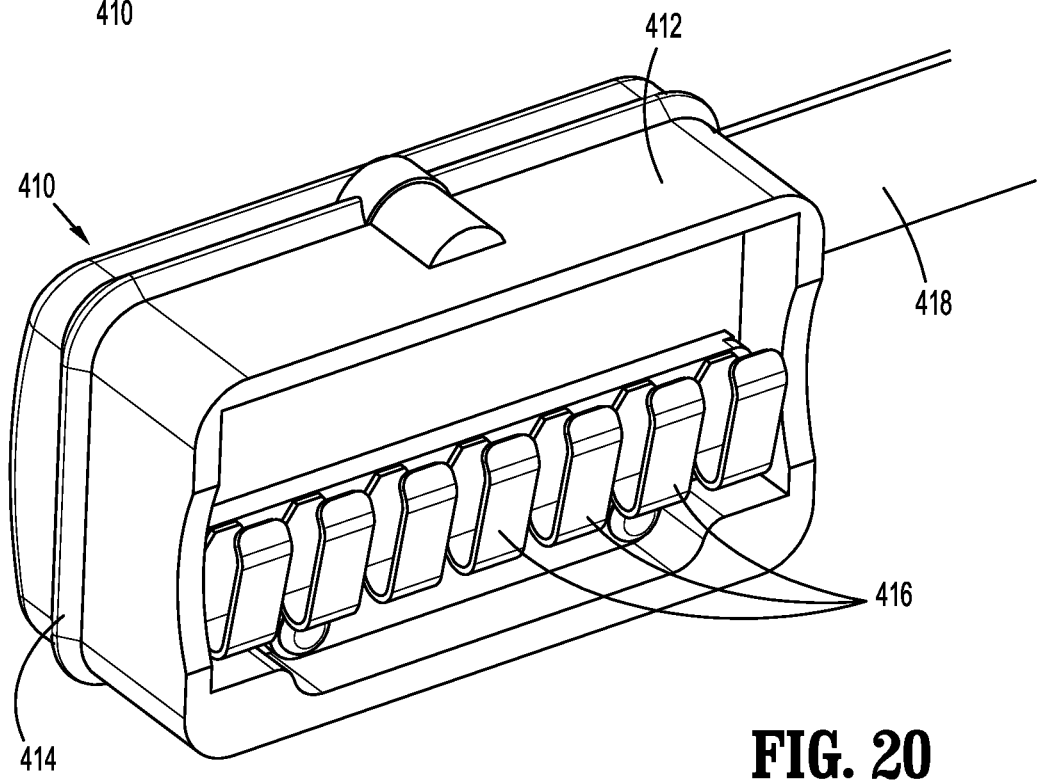
FIG. 20 is another perspective view of the electrical connector assembly of FIG. 19.
Figure 23:
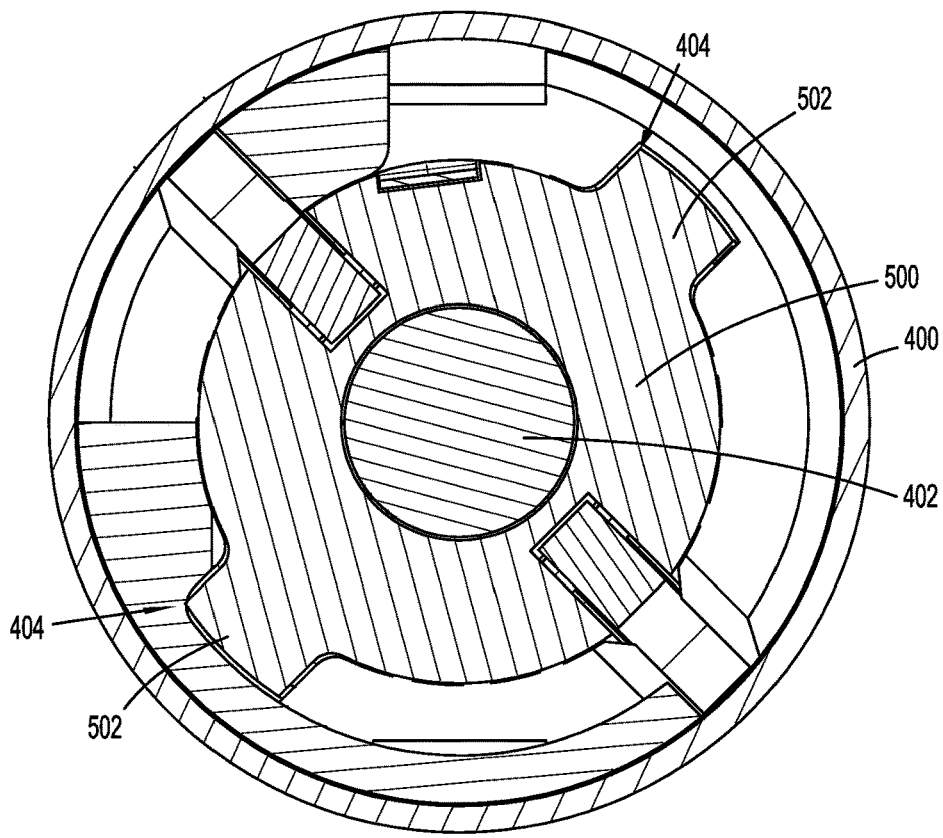
FIGS. 23-26 are enlarged, progressive cross-sectional views of the adapter and loading unit of FIG. 16 as taken along respective section lines 23-23, 24-24, 25-25 and 26-26 shown in FIG. 27, these views illustrating the loading unit and the adapter of FIG. 16 being coupled together.
Figure 24:
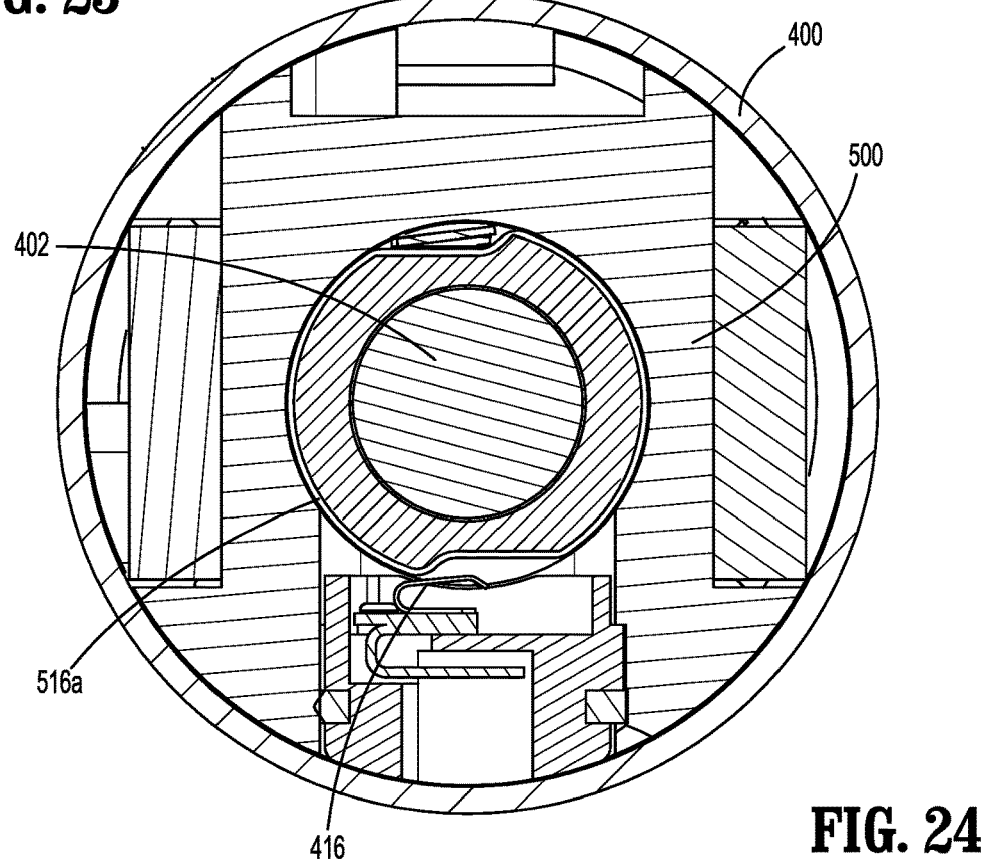
Figure 25:
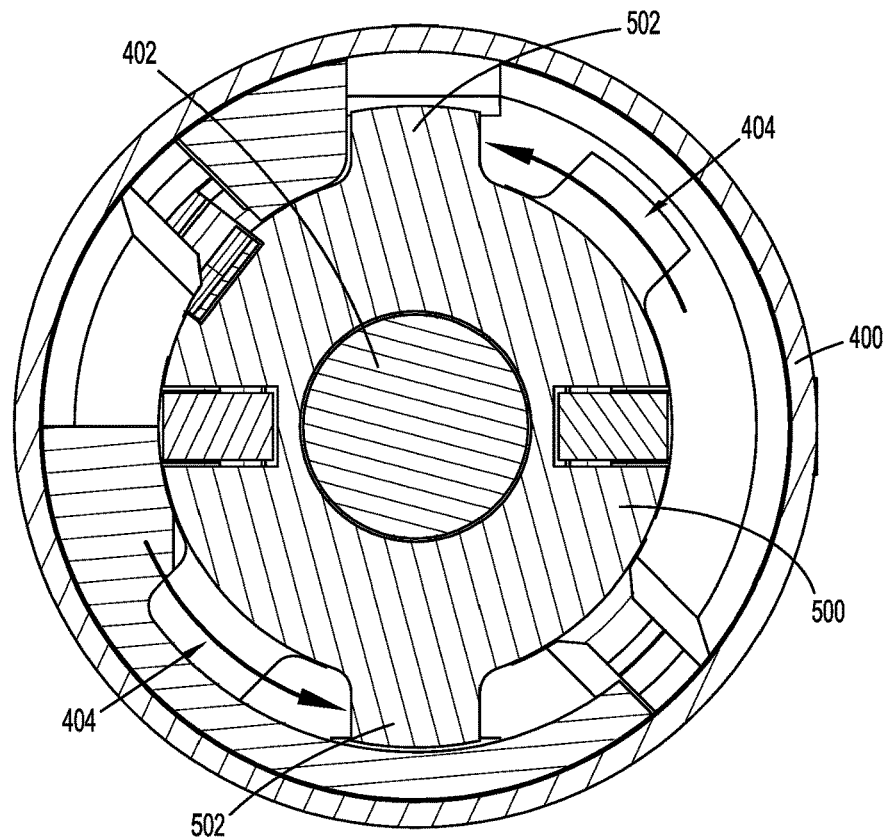
Figure 26:
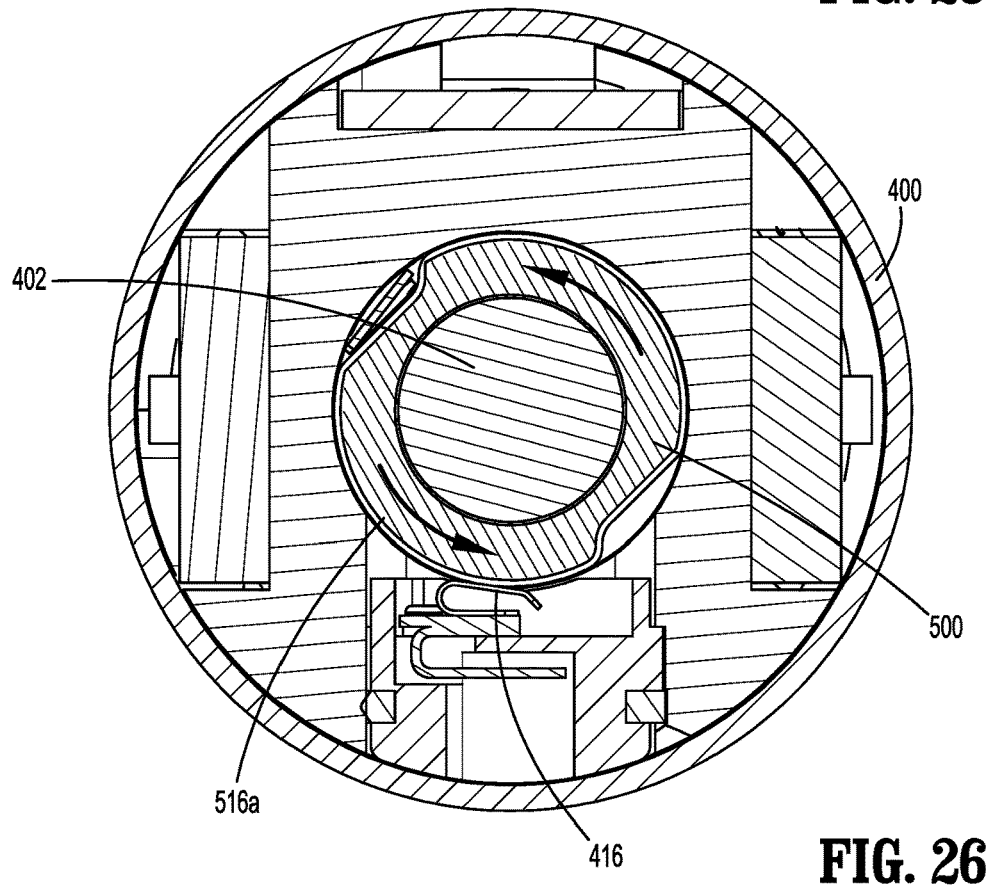
Figure 27:
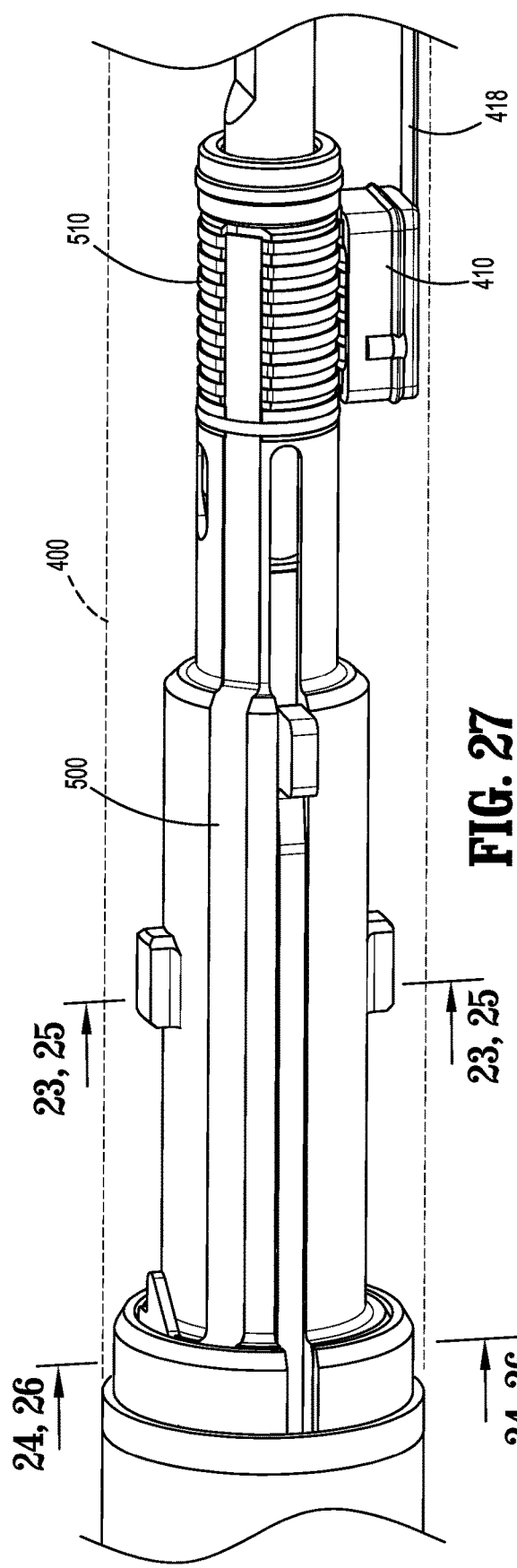
FIG. 27 is an enlarged, perspective view illustrating the loading unit and the adapter of FIG. 16 coupled together.
Figure 28:
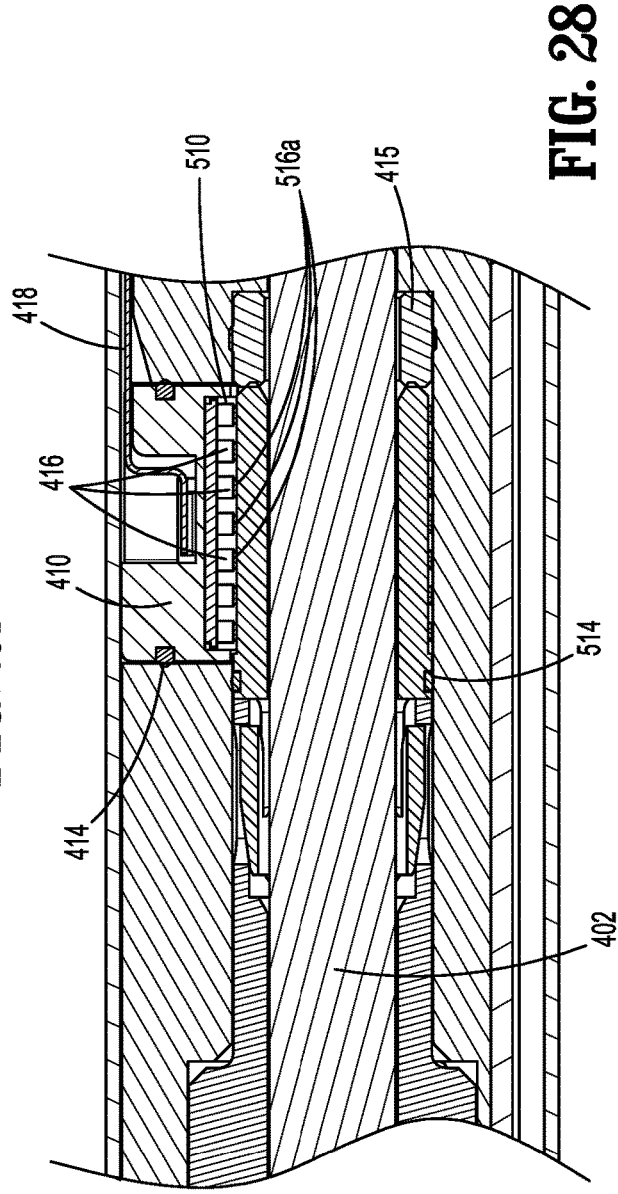
FIG. 28 is an enlarged view of the indicated area of detail shown in FIG. 17 when the adapter and loading unit of FIG. 16 are coupled together as seen in FIG. 27.
Figure 29:
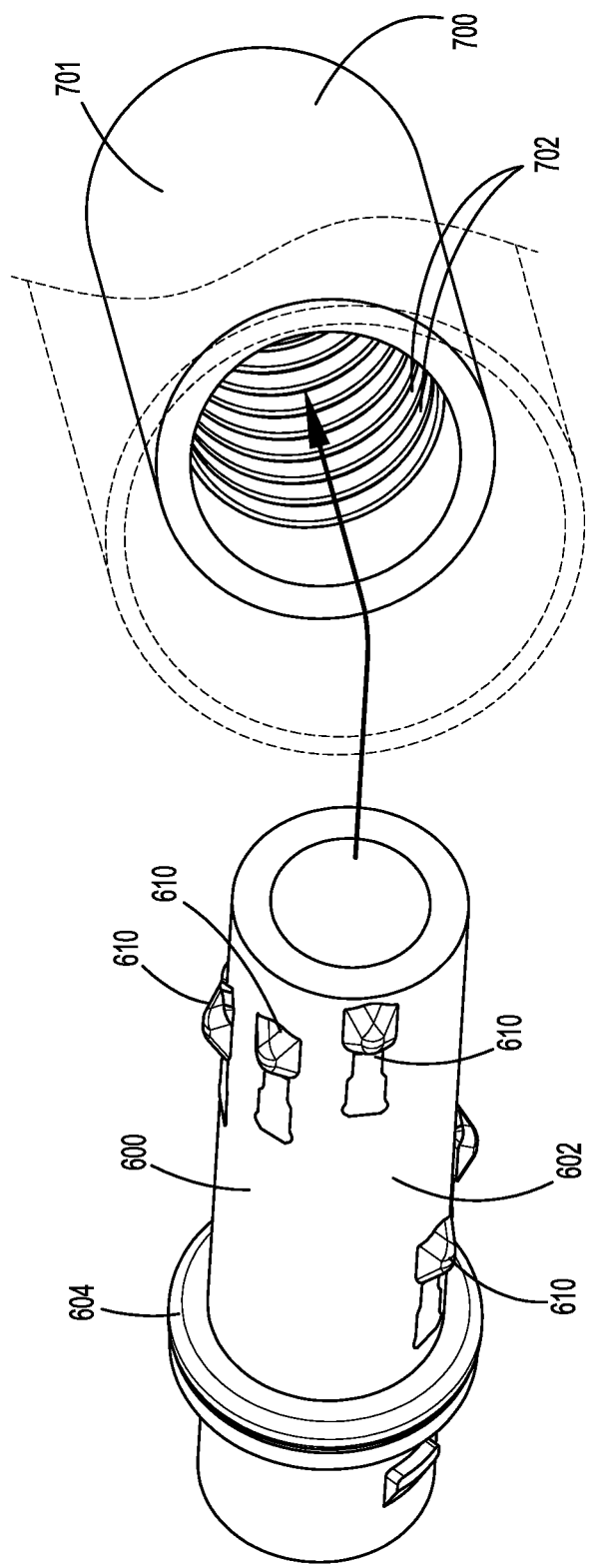
FIG. 29 is a perspective view, with parts separated, of yet another proximal end portion of a loading unit and yet another distal end portion of an adapter of the elongated shaft assembly of FIG. 1B.
Figure 30:
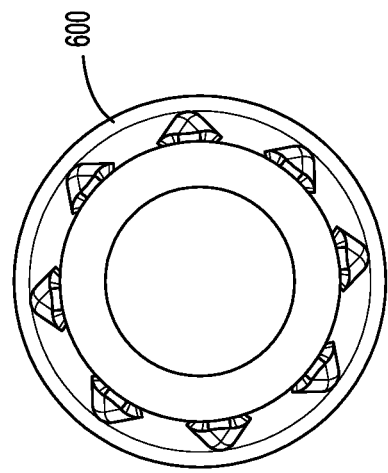
FIG. 30 is a front view of the proximal end portion of the loading unit of FIG. 29 with portions thereof removed and/or in phantom for clarity.
Figure 31:
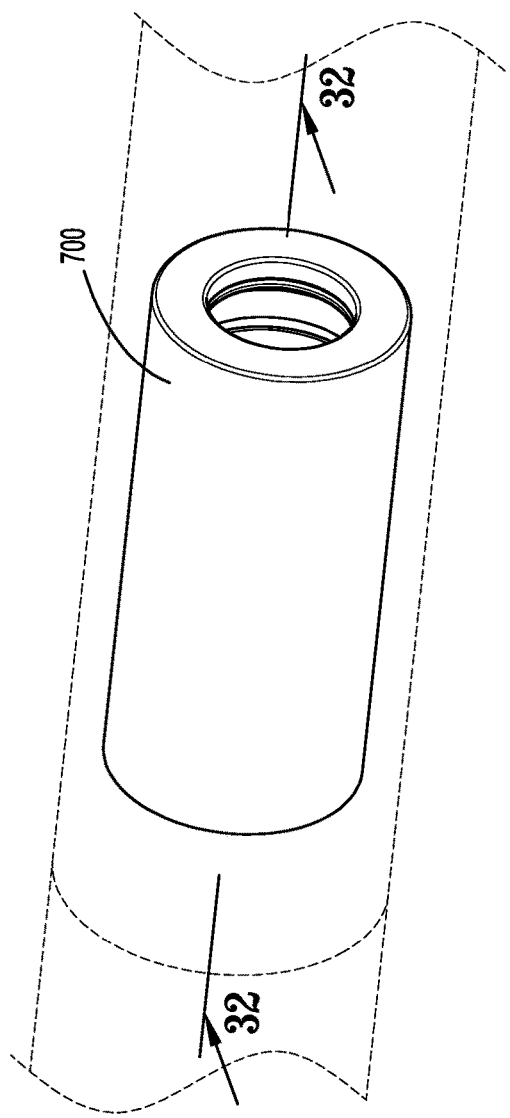
FIG. 31 is a perspective view of a portion of the adapter of FIG. 29 with portions thereof removed and/or in phantom for clarity.
Figure 32:
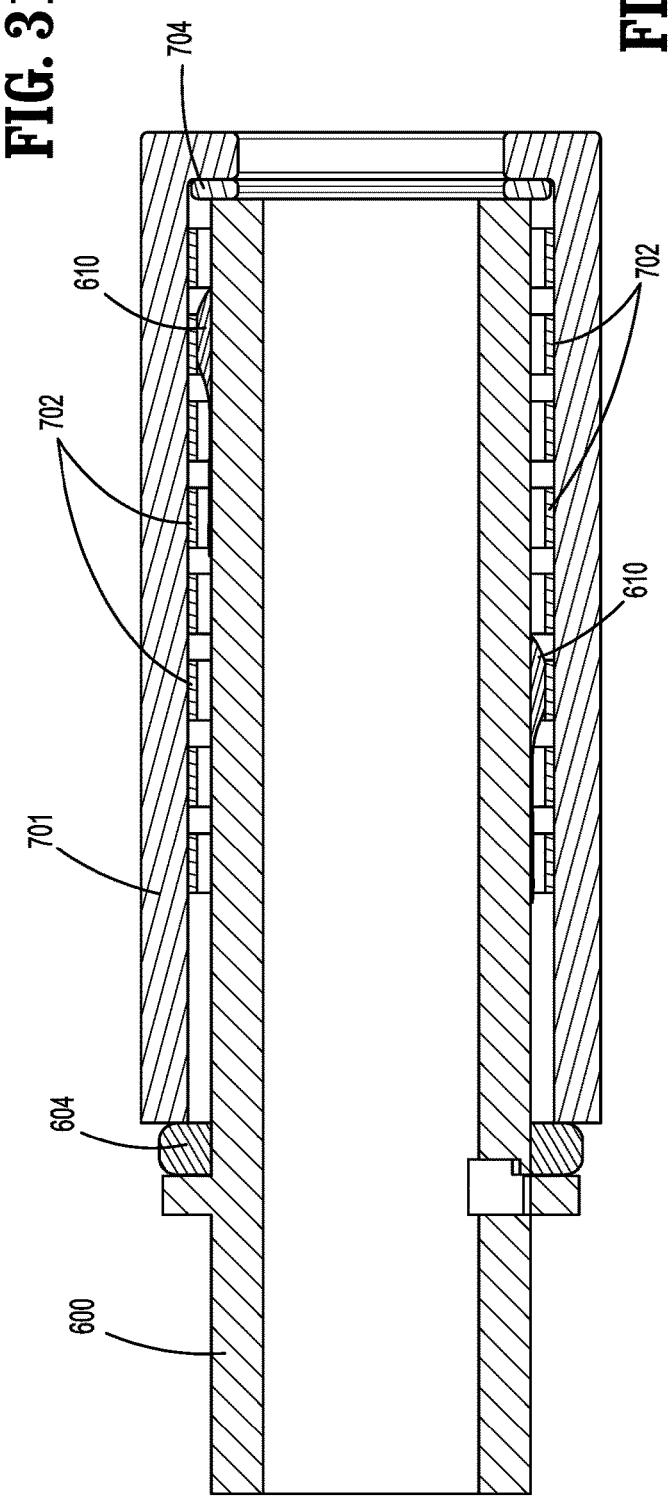
FIG. 32 is an enlarged, cross-sectional view of portions of the adapter and loading unit of FIG. 29 as taken along section line 32-32 shown in FIG. 31 when the adapter and loading unit are coupled together.
Figure 33:
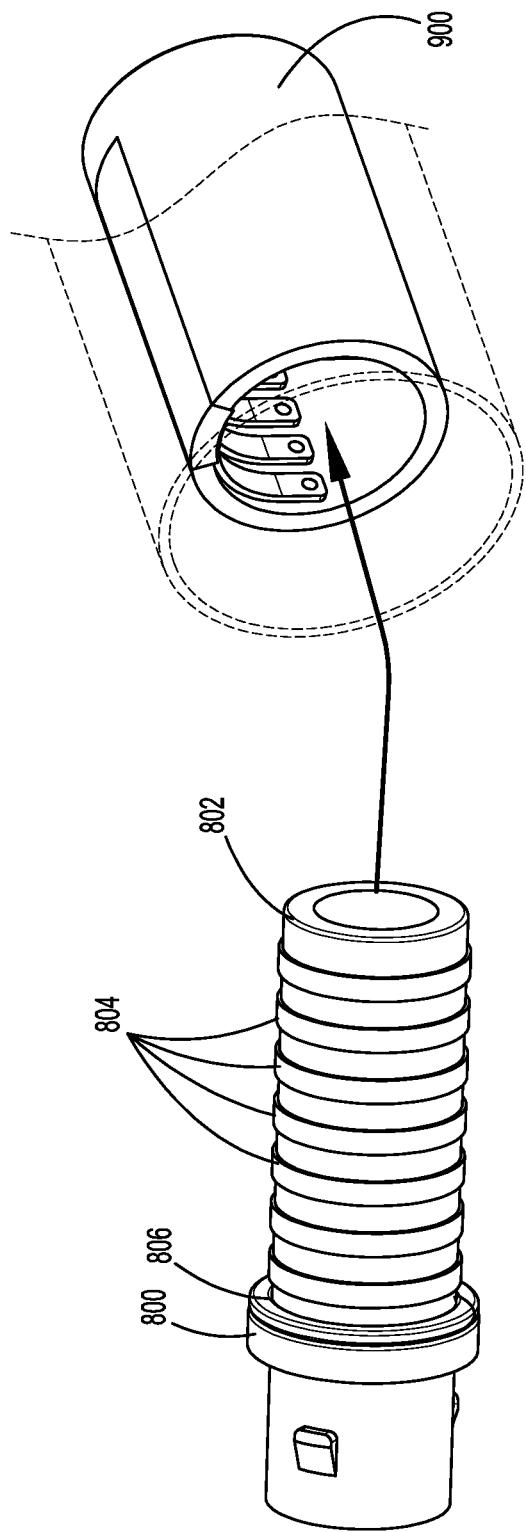
FIG. 33 is a perspective view, with parts separated, of still another proximal end portion of a loading unit of the elongated shaft assembly of FIG. 1B and still another distal end portion of an adapter of the elongated shaft assembly of FIG. 1B with portions thereof removed and/or in phantom for clarity.
Figure 34:
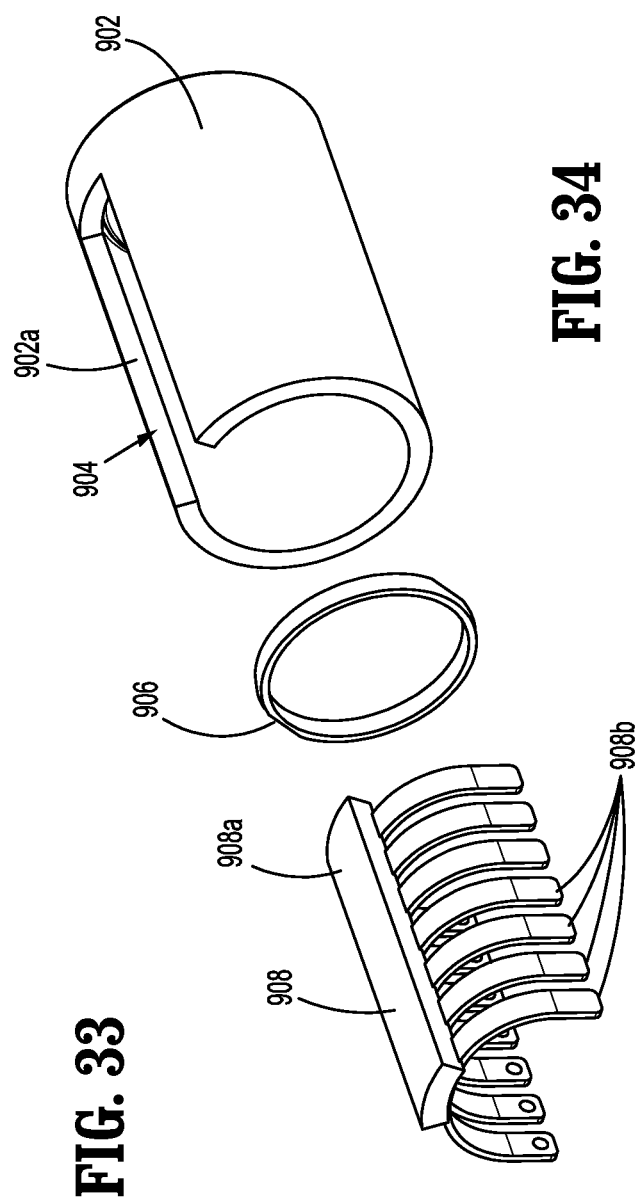
FIG. 34 is a perspective view, with parts separated, of an electrical assembly of the adapter of FIG. 33.

As best seen in FIGS. 19 and 20, adapter electrical connector assembly 410 includes a connector housing 412 and a peripheral seal 414 secured onto connector housing 412 (e.g., overmolded). Adapter electrical connector assembly 410 further includes a plurality of spring contacts 416, which are electrically conductive, supported in connector housing 412 and longitudinally spaced apart from one another. Spring contacts 416 are coupled to a flex cable 418 (e.g., soldered thereto).

With reference to FIGS. 21 and 22, loading unit electrical connector assembly 510 includes a connector housing 512 that has a tubular body 512a. Tubular body 512 defines snap-fit apertures 512b through a sidewall of tubular body 512a. Tubular body 512 further defines a cable channel 512c along an outer surface of tubular body 512a. Loading unit electrical connector assembly 510 further includes a seal 514 (e.g., an O-ring), an electrical coupler 516 onto which seal 514 mounts, and a flex cable 518. Electrical coupler 516 includes a plurality of longitudinally spaced apart contract rings 516a, each of which is electrically conductive, and a pair of snap-fit arms 516b flexibly mounted thereto. Snap-fit arms 516b are configured to snap-fit into snap-fit apertures 512b of tubular body 512 to secure electrical coupler 516 to tubular body 512 as seen in FIG. 22.

With reference to FIGS. 23-28, to electromechanically couple loading unit 500 to adapter assembly 400, loading unit 500 is axially inserted into adapter assembly 400 and rotated similar to loading unit 200 and adapter assembly 400, as detailed above, so that loading unit electrical connector assembly 510 and adapter electrical connector assembly 410 electrically couple together.

Turning now to FIGS. 29-32, according to yet another aspect, a loading unit electrical connector assembly 600 can be electrically coupled to an adapter electrical connector assembly 700. Loading unit electrical connector assembly 600 includes a plurality of sheet metal contacts 610, each of which is electrically conductive, angularly spaced about a tubular body 602 of loading unit electrical connector assembly 600 and seal 604 supported on tubular body 602. Sheet metal contacts 610 may be angularly and/or longitudinally spaced apart from one another. In aspects, sheet metal contacts 610 may be disposed in a spiral arrangement about tubular body 602. Adapter electrical connector assembly 700 includes a plurality of annular contact rings 702, each of which is electrically conductive. The annular contact rings 702 are longitudinally spaced apart along an inner surface of a tubular body 701 of adapter electrical connector assembly 700. Adapter electrical connector assembly 700 further includes a seal 704 supported therein.

With reference to FIGS. 33-36, according to still another aspect, a loading unit electrical connector assembly 800 can be electrically coupled to an adapter electrical connector assembly 900. Loading unit electrical connector assembly 800 includes a tubular body 802 supporting a plurality of contact rings 804, each of which is electrically conductive, at longitudinally spaced apart locations and a seal 806. Adapter electrical connector assembly 900 includes a tubular body 902 defining a cutout 904 that extends longitudinally along sidewall 902a of tubular body 902. Adapter electrical connector assembly 900 further includes a seal 906 and a contact insert assembly 908 that is receivable in cutout 907 of tubular body 902. Contact insert assembly 908 includes an elongate leg 908a and a plurality of arched contacts 908b, each of which is electrically conductive, longitudinally spaced apart along elongate leg 908a and receivable within tubular body 902 when elongate leg 908a is seated in cutout 904 of tubular body 902.

Further, the various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Moreover, the disclosed electronic structure such as the electronic assembly and/or controllers, can include any suitable electrical components for operating the disclosed surgical stapling apparatus or components thereof. Such electrical components can include, for example, one or more controllers and/or circuitry, which may include or be coupled to one or more printed circuit boards. As used herein, the term "controller" includes "processor," "digital processing device" and like terms, and are used to indicate a microprocessor or central processing unit (CPU). The CPU is the electronic circuitry within a computer that carries out the instructions of a computer program by performing the basic arithmetic, logical, control and input/output (I/O) operations specified by the instructions, and by way of non-limiting examples, include server computers. In some aspects, the controller includes an operating system configured to perform executable instructions. The operating system is, for example, software, including programs and data, which manages hardware of the disclosed surgical stapling apparatus and provides services for execution of applications for use with the disclosed surgical stapling apparatus. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. In some aspects, the operating system is provided by cloud computing.

In some aspects, the term "controller" may be used to indicate a device that controls the transfer of data from a computer or computing device to a peripheral or separate device and vice versa, and/or a mechanical and/or electro-mechanical device (e.g., a lever, knob, etc.) that mechanically operates and/or actuates a peripheral or separate device.

In aspects, the controller includes a storage and/or memory device. The storage and/or memory device is one or more physical apparatus used to store data or programs on a temporary or permanent basis. In some aspects, the controller includes volatile memory and requires power to maintain stored information. In various aspects, the controller includes non-volatile memory and retains stored information when it is not powered. In some aspects, the non-volatile memory includes flash memory. In certain aspects, the non-volatile memory includes dynamic random-access memory (DRAM). In some aspects, the non-volatile memory includes ferroelectric random access memory (FRAM). In various aspects, the non-volatile memory includes phase-change random access memory (PRAM). In certain aspects, the controller is a storage device including, by way of non-limiting examples, CD-ROMs, DVDs, flash memory devices, magnetic disk drives, magnetic tapes drives, optical disk drives, and cloud computing based storage. In various aspects, the storage and/or memory device is a combination of devices such as those disclosed herein.

In some aspects, the controller includes a display to send visual information to a user. In various aspects, the display is a cathode ray tube (CRT). In various aspects, the display is a liquid crystal display (LCD). In certain aspects, the display is a thin film transistor liquid crystal display (TFT-LCD). In aspects, the display is an organic light emitting diode (OLED) display. In certain aspects, on OLED display is a passive-matrix OLED (PMOLED) or active-matrix OLED (AMOLED) display. In aspects, the display is a plasma display. In certain aspects, the display is a video projector. In various aspects, the display is interactive (e.g., having a touch screen or a sensor such as a camera, a 3D sensor, a LiDAR, a radar, etc.) that can detect user interactions/gestures/responses and the like. In some aspects, the display is a combination of devices such as those disclosed herein.

The controller may include or be coupled to a server and/or a network. As used herein, the term "server" includes "computer server," "central server," "main server," and like terms to indicate a computer or device on a network that manages the surgical stapling apparatus, components thereof, and/or resources thereof. As used herein, the term "network" can include any network technology including, for instance, a cellular data network, a wired network, a fiber optic network, a satellite network, and/or an IEEE 802.11a/b/g/n/ac wireless network, among others.

In various aspects, the controller can be coupled to a mesh network. As used herein, a "mesh network" is a network topology in which each node relays data for the network. All mesh nodes cooperate in the distribution of data in the network. It can be applied to both wired and wireless networks. Wireless mesh networks can be considered a type of "Wireless ad hoc" network. Thus, wireless mesh networks are closely related to Mobile ad hoc networks (MANETs).

Although MANETs are not restricted to a specific mesh network topology, Wireless ad hoc networks or MANETs can take any form of network topology. Mesh networks can relay messages using either a flooding technique or a routing technique. With routing, the message is propagated along a path by hopping from node to node until it reaches its destination. To ensure that all its paths are available, the network must allow for continuous connections and must reconfigure itself around broken paths, using self-healing algorithms such as Shortest Path Bridging. Self-healing allows a routing-based network to operate when a node breaks down or when a connection becomes unreliable. As a result, the network is typically quite reliable, as there is often more than one path between a source and a destination in the network. This concept can also apply to wired networks and to software interaction. A mesh network whose nodes are all connected to each other is a fully connected network.

In some aspects, the controller may include one or more modules. As used herein, the term "module" and like terms are used to indicate a self-contained hardware component of the central server, which in turn includes software modules. In software, a module is a part of a program. Programs are composed of one or more independently developed modules that are not combined until the program is linked. A single module can contain one or several routines, or sections of programs that perform a particular task.

As used herein, the controller includes software modules for managing various aspects and functions of the disclosed surgical stapling apparatus or components thereof.

The disclosed surgical stapling apparatus may also utilize one or more controllers to receive various information and transform the received information to generate an output. The controller may include any type of computing device, computational circuit, or any type of processor or processing circuit capable of executing a series of instructions that are stored in memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

As can be appreciated, securement of any of the components of the disclosed apparatus can be effectuated using known securement techniques such welding, crimping, gluing, fastening, etc. Also, any of the disclosed structure can include any suitable conductive material (e.g., metallic), semi-conductive material (e.g., silicone), and/or non-conductive/insulative material (e.g., plastic).

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical stapling apparatus, comprising:
a housing assembly; and
an elongated shaft assembly selectively attachable to the housing assembly, the elongated shaft assembly including:
an adapter assembly extending distally to a distal tip housing, the distal tip housing supporting an adapter electrical connector assembly therein, the adapter electrical connector assembly including an adapter connector housing and an electronic ring assembly supported on a distal end portion of the adapter connector housing, the electronic ring assembly being electrically conductive; and
a loading unit selectively attachable to the adapter assembly and extending distally to an end effector supporting at least one sensor therein, the loading unit supporting a loading unit electrical connector assembly therein, the loading unit electrical connector assembly positioned to contact the adapter electrical connector assembly when the adapter assembly and the loading unit are coupled together to electrically couple the at least one sensor to the housing assembly.

2. The surgical stapling apparatus of claim 1, wherein the at least one sensor configured to measure data including thickness of tissue clamped by the end effector, clamp force of the end effector, or firing force of the end effector.

3. The surgical stapling apparatus of claim 1, wherein the adapter connector housing rotatably supports a firing rod therethrough.

4. The surgical stapling apparatus of claim 3, wherein the adapter connector housing includes a connector shaft that supports the electronic ring assembly thereon.

5. The surgical stapling apparatus of claim 4, wherein the connector shaft defines a plurality of annular ribs and a plurality of ring recesses disposed between the annular ribs, the plurality of ring recesses and the plurality of annual ribs positioned to support a plurality of contact rings of the electronic ring assembly in a longitudinally offset arrangement within the distal tip housing.

6. The surgical stapling apparatus of claim 5, wherein the plurality of contact rings is electrically coupled to a flex cable supported by a channel defined within the adapter connector housing.

7. The surgical stapling apparatus of claim 5, wherein the loading unit electrical connector assembly includes a loading unit connector housing that supports a plurality of spring contacts positioned to contact the plurality of contact rings of the electronic ring assembly.

8. The surgical stapling apparatus of claim 7, wherein the plurality of spring contacts is electrically coupled to the at least one sensor.

9. The surgical stapling apparatus of claim 1, wherein the adapter electrical connector assembly and the loading unit electrical connector assembly are sealed within elongated shaft assembly when electrically coupled together.

10. A surgical stapling apparatus, comprising:
a housing assembly;
an adapter assembly removably secured to the housing assembly and supporting an adapter electrical connector assembly therein, the adapter electrical connector assembly including an adapter connector housing and an electronic ring assembly supported on a distal end portion of the adapter connector housing, the electronic ring assembly being electrically conductive; and
a loading unit selectively electrically connectable to a distal end portion of the adapter assembly by relative translating and rotating movement between the loading unit and the adapter assembly, the loading unit supporting a loading unit electrical connector assembly, the loading unit electrical connector assembly positioned to receive the adapter electrical connector assembly to cause the adapter assembly and the loading unit to electrically couple together in response to the translating and rotating movement.

11. The surgical stapling apparatus of claim 10, wherein the loading unit extends to an end effector, the end effector supporting at least one sensor disposed in electrical communication with the adapter electrical connector assembly when the loading unit and the adapter assembly are coupled together.

12. The surgical stapling apparatus of claim 11, wherein the at least one sensor is configured to measure data including thickness of tissue clamped by the end effector, clamp force of the end effector, or firing force of the end effector.

13. The surgical stapling apparatus of claim 10, wherein the adapter connector housing includes a connector shaft that supports the electronic ring assembly thereon.

14. The surgical stapling apparatus of claim 13, wherein the connector shaft defines a plurality of annular ribs and a plurality of ring recesses disposed between the annular ribs, the plurality of ring recesses and the plurality of annual ribs positioned to support a plurality of contact rings of the electronic ring assembly in a longitudinally offset arrangement within a distal tip housing of the distal end portion of the adapter assembly.

15. The surgical stapling apparatus of claim 14, wherein the plurality of contact rings is electrically coupled to a flex cable supported by a channel defined within the adapter connector housing.

16. The surgical stapling apparatus of claim 14, wherein the loading unit electrical connector assembly includes a loading unit connector housing that supports a plurality of spring contacts longitudinally offset from one another and positioned to contact the plurality of contact rings of the electronic ring assembly.

17. The surgical stapling apparatus of claim 16, wherein the plurality of spring contacts is electrically coupled to the at least one sensor.

18. The surgical stapling apparatus of claim 10, wherein the loading unit defines a lug channel positioned to receive a lug of the adapter assembly, the lug channel having a longitudinally-extending portion to enable translating movement of the lug therethrough and a transverse portion to enable rotating movement of the lug therethrough.

* * * * *